US010472548B2

(12) United States Patent
Champagne et al.

(10) Patent No.: US 10,472,548 B2
(45) Date of Patent: Nov. 12, 2019

(54) DIENE/DIENOPHILE COUPLES AND THERMOSETTING RESIN COMPOSITIONS HAVING REWORKABILITY

(71) Applicant: Henkel IP & Holding GmbH, Duesseldorf (DE)

(72) Inventors: Timothy M. Champagne, Orange, AZ (US); Laxmisha M. Sridhar, Monmouth Junction, NJ (US); Jonathan B. Israel, Carson, CA (US); Philip T. Klemarczyk, Canton, CT (US); XianMan Zhang, Cheshire, CT (US); Benny E. Jordan, Corona, CA (US)

(73) Assignee: Henkel IP & Holding GmbH, Duesseldorf (DE)

( * ) Notice: Subject to any disclaimer, the term of this patent is extended or adjusted under 35 U.S.C. 154(b) by 153 days.

(21) Appl. No.: 15/795,501

(22) Filed: Oct. 27, 2017

(65) Prior Publication Data

US 2018/0155588 A1 Jun. 7, 2018

Related U.S. Application Data

(60) Division of application No. 14/857,870, filed on Sep. 18, 2015, now Pat. No. 9,938,437, which is a continuation of application No. PCT/US2014/031453, filed on Mar. 21, 2014.

(60) Provisional application No. 61/804,232, filed on Mar. 22, 2013.

(51) Int. Cl.
| | |
|---|---|
| *C09J 163/00* | (2006.01) |
| *C08L 63/00* | (2006.01) |
| *H01L 23/29* | (2006.01) |
| *H01L 21/56* | (2006.01) |
| *C08K 5/092* | (2006.01) |
| *C08F 283/10* | (2006.01) |
| *C07C 33/12* | (2006.01) |
| *C07C 69/54* | (2006.01) |
| *C07C 69/753* | (2006.01) |
| *C07D 303/16* | (2006.01) |
| *C07D 303/28* | (2006.01) |
| *C09J 163/04* | (2006.01) |
| *H01L 23/31* | (2006.01) |
| *H01L 23/498* | (2006.01) |
| *C08G 59/22* | (2006.01) |
| *C08G 59/24* | (2006.01) |
| *C08G 59/40* | (2006.01) |
| *C08G 59/50* | (2006.01) |
| *C08G 59/56* | (2006.01) |
| *C08L 53/02* | (2006.01) |
| *C08L 79/08* | (2006.01) |

(52) U.S. Cl.
CPC ............. *C09J 163/00* (2013.01); *C07C 33/12* (2013.01); *C07C 69/54* (2013.01); *C07C 69/753* (2013.01); *C07D 303/16* (2013.01); *C07D 303/28* (2013.01); *C08F 283/10* (2013.01); *C08G 59/226* (2013.01); *C08G 59/24* (2013.01); *C08G 59/4021* (2013.01); *C08G 59/5073* (2013.01); *C08G 59/56* (2013.01); *C08K 5/092* (2013.01); *C08L 53/02* (2013.01); *C08L 63/00* (2013.01); *C09J 163/04* (2013.01); *H01L 21/563* (2013.01); *H01L 23/293* (2013.01); *H01L 23/3142* (2013.01); *H01L 23/49838* (2013.01); *C07C 2603/68* (2017.05); *C08L 79/085* (2013.01); *H01L 2224/16225* (2013.01); *H01L 2224/32225* (2013.01); *H01L 2224/73204* (2013.01); *H01L 2924/15311* (2013.01)

(58) Field of Classification Search
CPC ....... C09J 163/00; C08L 63/00; C08L 79/085; C08L 53/02
See application file for complete search history.

(56) References Cited

U.S. PATENT DOCUMENTS

| | | | |
|---|---|---|---|
| 2,992,196 A | 7/1961 | Ilardo et al. | |
| 3,435,003 A | 3/1969 | Craven | |
| 3,826,760 A * | 7/1974 | Takeshita | ............... C08G 59/24 526/273 |
| 3,890,253 A * | 6/1975 | Takeshita | ............... C08G 59/24 525/383 |
| 4,503,219 A | 3/1985 | Reffert et al. | |
| 4,619,977 A | 10/1986 | Qaderi | |
| 5,268,489 A | 12/1993 | Koleske et al. | |
| 5,512,613 A | 4/1996 | Afzali-Ardakani et al. | |
| 5,560,934 A | 10/1996 | Afzali-Ardakani et al. | |

(Continued)

FOREIGN PATENT DOCUMENTS

| | | |
|---|---|---|
| EP | 0093910 | 11/1983 |
| JP | 02-108657 | 4/1990 |

(Continued)

OTHER PUBLICATIONS

International Search Report issued in connection with International Application No. PCT/2014/031453 dated Aug. 12, 2014.

*Primary Examiner* — Margaret G Moore
(74) *Attorney, Agent, or Firm* — Steven C. Bauman

(57) ABSTRACT

Thermosetting resin compositions are provided that are useful for mounting onto a circuit board semiconductor devices, such as chip size or chip scale packages ("CSPs"), ball grid arrays ("BGAs"), land grid arrays ("LGAs") and the like (collectively, "subcomponents"), or semiconductor chips. Reaction products of the compositions are controllably reworkable when subjected to appropriate conditions.

8 Claims, 10 Drawing Sheets

(56) References Cited

U.S. PATENT DOCUMENTS

| | | |
|---|---|---|
| 5,605,999 A | 2/1997 | Chu et al. |
| 5,659,203 A | 8/1997 | Call et al. |
| 5,760,337 A | 6/1998 | Lyer et al. |
| 5,807,937 A | 9/1998 | Matyjaszewski et al. |
| 5,872,158 A | 2/1999 | Kuczynski |
| 5,932,682 A | 8/1999 | Buchwalter et al. |
| 5,948,922 A | 9/1999 | Ober et al. |
| 6,057,381 A | 5/2000 | Ma et al. |
| 6,172,141 B1 | 1/2001 | Wong et al. |
| 6,197,122 B1 | 3/2001 | Ober et al. |
| 6,313,250 B1 * | 11/2001 | Blum .................. C08G 59/1455 526/202 |
| 6,337,384 B1 | 1/2002 | Loy et al. |
| 6,498,260 B2 | 12/2002 | Wang et al. |
| 6,570,029 B2 | 5/2003 | Wang et al. |
| 6,657,031 B1 | 12/2003 | Crane et al. |
| 6,916,890 B1 | 7/2005 | Woods et al. |
| 7,012,120 B2 | 3/2006 | Klemarczyk et al. |
| 7,109,061 B2 | 9/2006 | Crane et al. |
| 8,075,721 B2 | 12/2011 | Ji et al. |
| 8,820,549 B1 | 9/2014 | Estrada |
| 9,938,437 B2 * | 4/2018 | Champagne ........... C08K 5/092 |
| 2006/0223937 A1 * | 10/2006 | Herr ....................... C08G 59/24 524/556 |
| 2007/0117917 A1 * | 5/2007 | Herr ....................... C08G 59/24 524/556 |
| 2009/0111737 A1 | 4/2009 | Christensen et al. |
| 2010/0331493 A1 | 12/2010 | Percec |
| 2011/0060157 A1 | 3/2011 | Glaser et al. |
| 2012/0160828 A1 * | 6/2012 | Bowman ............. B29C 65/3612 219/603 |
| 2013/0244179 A1 * | 9/2013 | Bowman ................ C08G 61/12 430/283.1 |
| 2013/0317156 A1 | 11/2013 | Yu |

FOREIGN PATENT DOCUMENTS

| | | |
|---|---|---|
| JP | 2002540235 | 11/2002 |
| JP | 2003502484 | 1/2003 |
| JP | 2003183348 | 7/2003 |
| JP | 2006193628 | 7/2006 |
| WO | 0056799 | 9/2000 |

* cited by examiner

DIENE/DIENOPHILE COUPLES AND THERMOSETTING RESIN COMPOSITIONS HAVING REWORKABILITY

This application is a DIV of U.S. Ser. No. 14/857,870, Sep. 18, 2015, now U.S. Pat. No. 9,938,437.

BACKGROUND

Field

Thermosetting resin compositions are provided that are useful for mounting onto a circuit board semiconductor devices, such as chip size or chip scale packages ("CSPs"), ball grid arrays ("BGAs"), land grid arrays ("LGAs") and the like (collectively, "subcomponents"), or semiconductor chips. Reaction products of the compositions are controllably reworkable when subjected to appropriate conditions.

Brief Description of Related Technology

The popularity of hand held display devices has made their demand increase dramatically in recent years. Manufacturing throughout has consequently been challenged to increase in order to meet the growing demand. One area that is particularly troublesome for manufacturers is the treatment and handling of defective subcomponents. For instance, during the manufacture of a circuit board subassembly a multitude of semiconductor devices are electrically connected to the board. The board may then be tested to evaluate function. Sometimes the board fails. In such cases, it is desirable to identify the semiconductor device that caused the failure, remove it from the board and reuse the board with the remaining functioning semiconductor devices.

Ordinarily, subcomponents are connected to electrical conductors (or, metallization) on a circuit board by the use of a solder connection. However, when the resulting subassembly is exposed to thermal cycling, vibration, distortion or is dropped, the reliability of the solder connection between the circuit board and the subcomponent(s) often become(s) suspect. After a subcomponent is mounted on a circuit board, the space between the subcomponent and the circuit board is ordinarily filled with a sealant resin (commonly referred to as underfill sealant) in order to relieve stresses caused by thermal cycling, thereby improving heat shock properties and enhancing the reliability of the assembled structure.

However, since thermosetting resin compositions that form cross linked networks when cured are typically used as the underfill sealant, in the event of a failure after the subcomponent is mounted on the circuit board, it is difficult to replace the subcomponent without destroying or scrapping the so-formed subassembly in its entirety.

Notwithstanding the state-of-the-art, it would be desirable for an underfilling sealant to flow rapidly by capillary action in the underfill space between the subcomponent or semiconductor chip and the circuit board; to cure rapidly under low temperature conditions; to provide good productivity and thermal shock resistance, while allowing the substrates with which it is to be used to be readily processed and easily separated from a defective subcomponent or semiconductor chip under conditions that do not compromise the integrity of the remaining subcomponents or semiconductor chips remaining on the substrate or the substrate itself; and to be reworkable in the event of failure of the defective subcomponent or semiconductor chip once assembled onto the circuit board.

SUMMARY

Thermosetting resin compositions useful as an underfill sealant are provided. The composition enables a subcomponent or semiconductor chip to be securely connected to a circuit board by short-time heat curing and with good productivity, which demonstrates excellent heat shock properties (or thermal cycle properties), and permits the subcomponent or semiconductor chip to be readily removed from the circuit board in the event of subcomponent or semiconductor chip or connection failure.

Reaction products of these compositions are capable of being controllably reworked through the softening and loss of their adhesiveness, such as by exposure to a temperature condition greater than a temperature condition used to cure the composition.

More specifically, the inventive compositions provide a curable resin component and a curative, and in one aspect a diene/dienophile couple functionalized with at least two carboxylic acid groups and in another aspect a diene/dienophile couple functionalized with at least two groups (at least one of which not being a carboxylic acid group) reactive with the curable resin component.

In each of these aspects, the reaction products of inventive compositions are controllably degradable upon exposure to a temperature condition greater than a temperature condition used to cure the composition.

Although the inventive compositions are curable at a relatively low temperature in a short period of time, cured reaction products thereof have excellent heat shock properties and, moreover, can be easily split by the application of force under heated conditions. That is, subcomponents or semiconductor chips attached to circuit boards by cured reaction products of the inventive thermosetting resin compositions can be easily removed by heating the reaction product.

By using the inventive compositions, subcomponents or semiconductor chips can be securely connected to a circuit board by short-time heat curing and with good productivity, with the resulting subassembly demonstrating excellent heat shock properties (or, thermal cycle properties). Moreover, in the event of failure, the subcomponent or semiconductor chip can be easily removed. This makes it possible to reuse the circuit board, thereby achieving an improvement in the yield of the production process and reducing production cost.

The benefits and advantages of the present invention will become more readily apparent after a reading the "Detailed Description", with reference to the figures.

DETAILED DESCRIPTION

Figure 1:
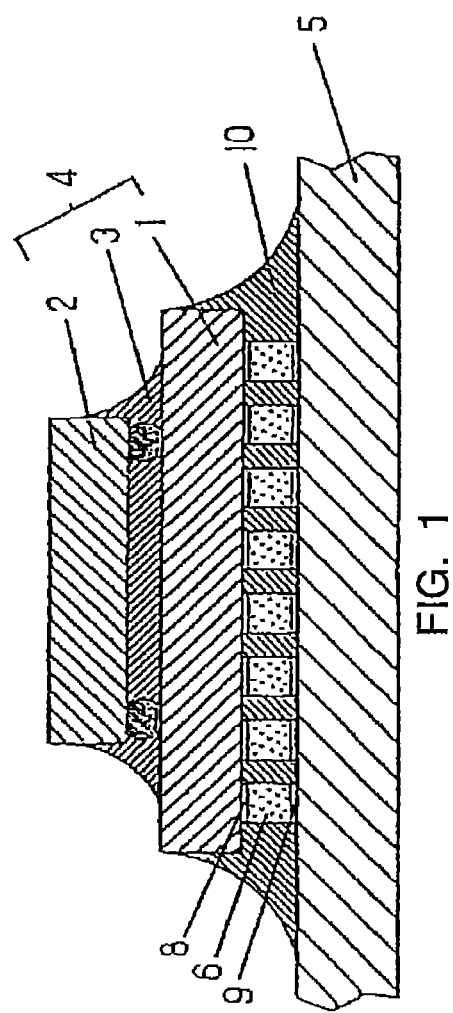
FIG. 1 depicts a cross-sectional view showing an example of a semiconductor device in which the thermosetting resin composition of the present invention is used.

As noted above, the inventive compositions provide a curable resin component and a curative, and in one aspect a diene/dienophile couple functionalized with at least two carboxylic acid groups and in another aspect a diene/dienophile couple functionalized with at least two groups (at least one of which not being a carboxylic acid group) reactive with the curable resin component.

The diene/dienophile couple may be selected from dicyclopentadiene, cyclopentadiene-maleimide, cyclopentadiene-maleate, cyclopentadiene-fumarate, cyclopentadiene-(meth) acrylate, cyclopentadiene-crotonate, cyclopentadiene-cinnamate, cyclopentadiene-(meth)acrylamide and furan-maleimide may be chosen.

The diene of the diene/dienophile couple may be selected from acyclic 1,3-diene, cyclopentadiene, cyclohexadiene, furan, fulvene, pyrrole, naphthalene and anthracene.

The dienophile of the diene/dienophile couple may be selected from cyclopentadiene, maleimide, isomaleimide, citraconimide, itaconimide, maleate, crotonate, cinnamate, fumarate, (meth)acrylate, cyanoacrylate, benzoquinone, benzoquinone oxime, benzoquinone imine, naphthaquinone, alkylidene malonate, (meth)acrylamide, and alkyne containing electron withdrawing groups. Notably, cyclopentadiene may be thought of as both a diene and a dienophile.

The diene/dienophile couple may be embraced by compounds within structure I

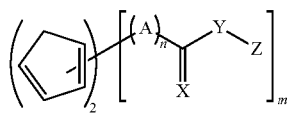

I where X is $CH_2$, O, S, or NR, where R is H, alkyl, aryl or aralkyl; Y is O, S or NR, where R is H, alkyl, aryl or aralkyl; A is alkylene; Z is a H, (meth)acryloyl, glycidyl or a group containing polymerizable functionality, such as epoxy (other than glycidyl), episulfide, (meth)acrylate (other than (meth) acryloyl), (meth)acrylamide, maleimide, maleate, fumarate, cinnamate, crotonate, oxetane, thioxetane, allyl, styrenics, oxazine (such as benzoxazine), oxazoline, N-vinylamide and vinyl ether; n is 0 or 1; and m is 2-4.

The diene/dienophile couple may be embraced by compounds within structure II

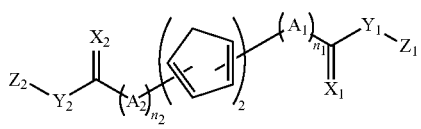

II where $X_1$ and $X_2$ are the same or different, and are each independently selected from $CH_2$, O, S, or NR, where R is H, alkyl, aryl or aralkyl; $Y_1$ and $Y_2$ are the same or different and are each independently selected from O, S or NR, where R is H, alkyl, aryl or aralkyl; $A_1$ and $A_2$ are the same or different and are each independently alkylene; $Z_1$ and $Z_2$ are the same or different and are each independently selected from H, (meth)acryloyl, glycidyl, or one or more of groups containing polymerizable functionalities, such as epoxy (other than glycidyl), episulfide, (meth)acrylate (other than (meth)acryloyl), (meth)acrylamide, maleimide, maleate, fumarate, cinnamate, crotonate, oxetane, thioxetane, allyl, styrenics, oxazine (such as benzoxazine), oxazoline, N-vinylamide and vinyl ether; and $n_1$ and $n_2$ are the same or different and are each independently 0 or 1.

Compounds within structure I include isomers of the dicarboxylic acid of dicyclopendadienyl ("DCPD") having structures IA-IF where X is O, Y is O, Z is H and n is 0:

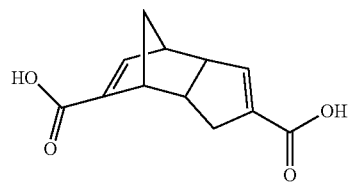

IA

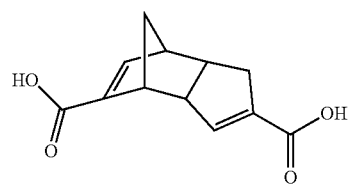

IB

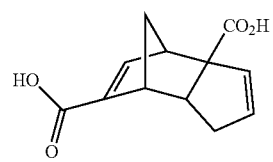

IC

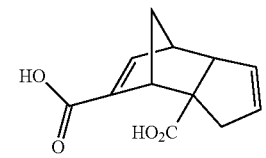

ID

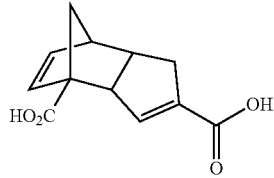

IE

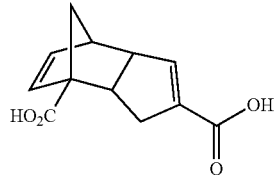

IF

Representative examples of compounds within structure I where X is O, Y is O, Z is a group containing polymerizable functionality and n is 0 include compounds represented by structures A-E (for convenience compounds A-E are depicted using a single structure but other isomers similar to those shown for IA-IF are also possible with compounds A-E):
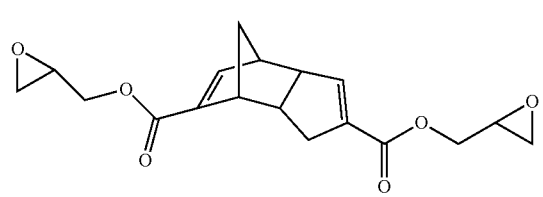
A
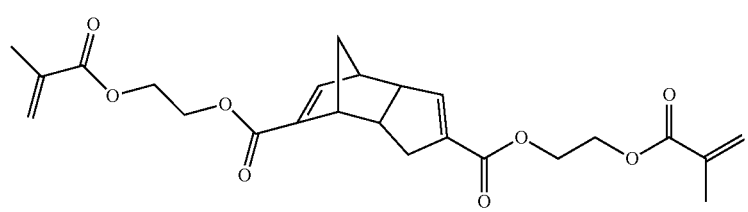
B
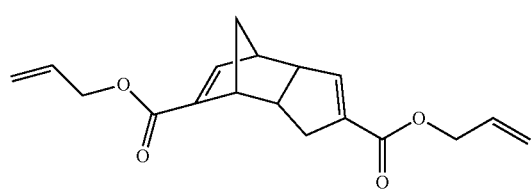
C
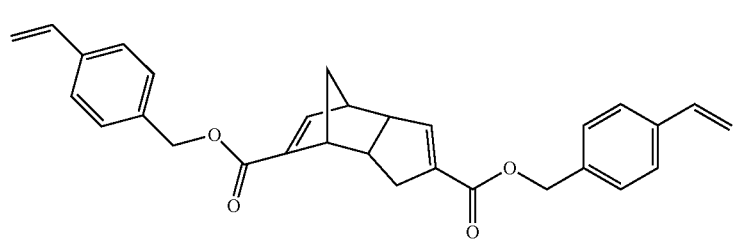
D
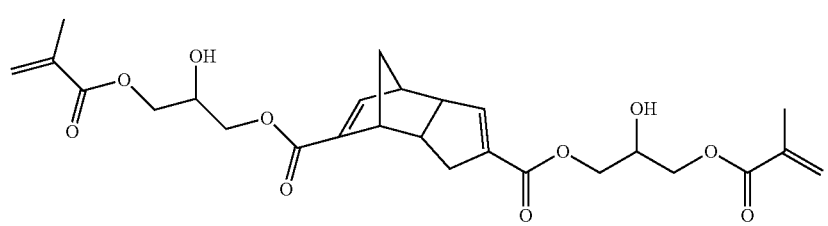
E In still another embodiment, the invention provides compounds within structure I that have been chain extended through reaction of DCPD dicarboxylic acid with difunctional epoxy or multifunctional epoxy resin in a controlled way; or by the reaction of a dicarboxylic acid with DCPD diepoxide (structure A).

Representative examples of the chain extended version of compounds within structure I where X is O, Y is O and Z is group containing polymerizable functionality include structures F-H:

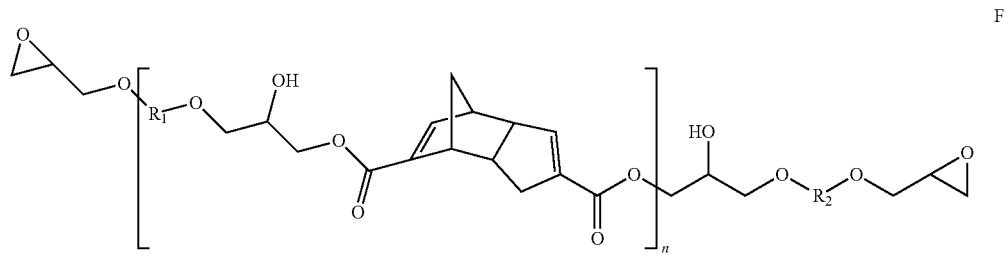

F where $R_1$ and $R_2$ may be same or different and are each independently selected from backbones of a difunctional epoxy resin or multifunctional epoxy resin, and n is 1-10;

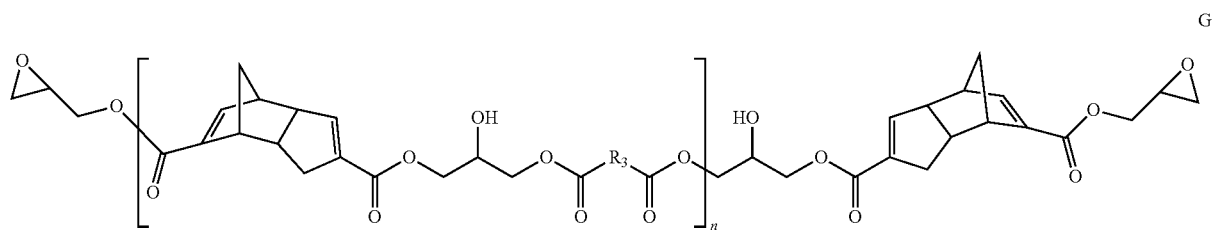

G

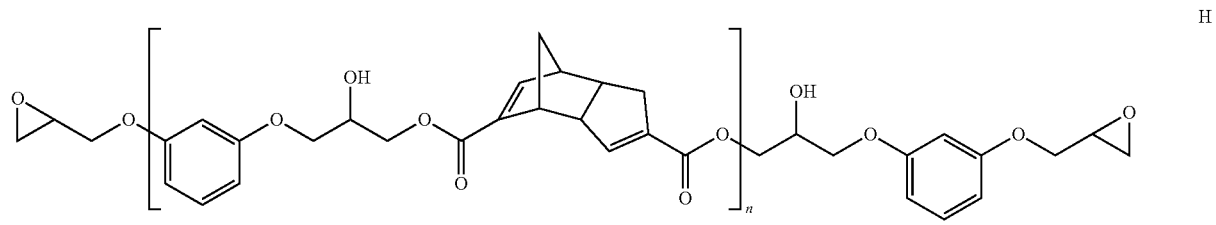

H where in structure G, $R_3$ is a dicarboxylic acid backbone; and in structure G and H, n is 1-10. These chain extended structures F-H can have head-head, head-tail or tail-head arrangements of DCPD units within the structures.

Representative examples of compounds within structure I where X is $CH_2$, Y is O, A is $CH_2$, n is 1, and Z is H, (meth)acryloyl or glycidyl functionality include structures J-L, respectively:

J

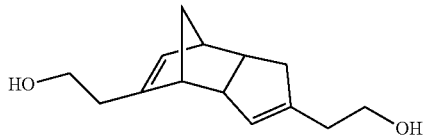

when Z is H;

K

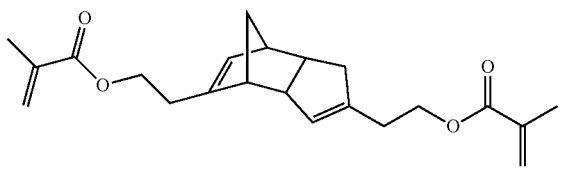

when Z is (methacryloyl);

L

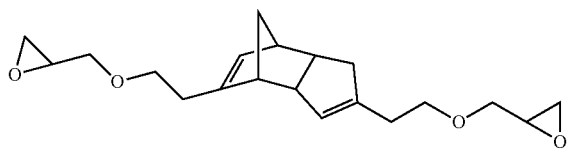

when Z is glycidyl.

In still yet another embodiment, compounds made from dicarboxylic acids of DCPD and having been reacted to form compounds derivatized to have different functionality groups are provided. An example of such a compound includes Representative examples of compounds within structure II where $X_1$ and $X_2$ are each O, $Y_1$ and $Y_2$ are each O, $A_1$ and $A_2$ are each 0, $n_1$ and $n_2$ are each 0, and $Z_1$ is epoxy and $Z_2$ is (meth)acrylate, include structure M:

M

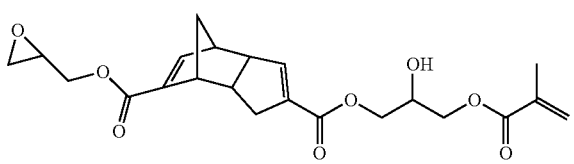

Of course, DCPD derivatives within structure I and II may also be used together with a curable resin component and a curative to form a thermosetting resin composition.

For instance, in another aspect, the thermosetting resin composition broadly includes a curable resin component and compounds within structure I

I

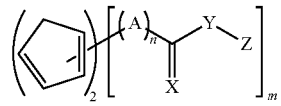

where X is $CH_2$, O, S, or NR, where R is H, alkyl, aryl or aralkyl; Y is O, S or NR, where R is H, alkyl, aryl or aralkyl; A is alkylene; Z is H, (meth)acryloyl, glycidyl or a group containing polymerizable functionality, such as epoxy (other than glycidyl), episulfide, (meth)acrylate (other than (meth)acryloyl), (meth)acrylamide, maleimide, maleate, fumarate, cinnamate, crotonate, oxetane, thioxetane, allyl, styrenics, oxazoline, oxazoline, N-vinylamide and vinyl ether; n is 0 or 1; and m is 2-4;
and/or
compounds within structure II:

II

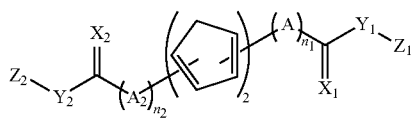

where $X_1$ and $X_2$ are the same or different, and are each independently selected from $CH_2$, O, S, or NR, where R is H, alkyl, aryl or aralkyl; $Y_1$ and $Y_2$ are the same or different and are each independently selected from O, S or NR, where R is H, alkyl, aryl or aralkyl; $A_1$ and $A_2$ are the same or different and are each independently alkylene; $Z_1$ and $Z_2$ are the same or different and are each independently selected from H, (meth)acryloyl, glycidyl, or one or more of groups containing polymerizable functionalities, such as epoxy (other than glycidyl), episulfide, (meth)acrylate (other than (meth)acryloyl), (meth)acrylamide, maleimide, maleate, fumarate, cinnamate, crotonate, oxetane, thioxetane, allyl, styrenics, oxazine (such as benzoxazine), oxazoline, N-vinylamide and vinyl ether; and $n_1$ and $n_2$ are the same or different and are each independently 0 or 1.

Compounds within structure I can be used as a curative or a fluxing agent, particularly where Z is hydrogen. Where Z (and/or $Z_1$ and/or $Z_2$) is a group containing polymerizable functionality, compounds within structure I and/or II are useful as coreactants for the curable resin component.

In addition, the composition may include one or more of a rubber toughening agent, an adhesion promoter, a wetting agent, a colorant, a defoaming agent, and a flowability agent.

The curable resin component may include bisphenol based epoxy resins, such as bisphenol A, bisphenol F, or bisphenol S epoxy resins, or combinations thereof. In addition, two or more different bisphenol epoxy resins within the same type of resin (such A, F or S) may be used.

Commercially available examples of the bisphenol epoxy resins desirable for use herein include bisphenol-F-type epoxy resins (such as RE-404-S from Nippon Kayaku, Japan, and EPICLON 830 (RE1801), 830S (RE1815), 830A (RE1826) and 830W from Dai Nippon Ink & Chemicals, Inc., and RSL 1738 and YL-983U from Resolution) and bisphenol-A-type epoxy resins (such as YL-979 and 980 from Resolution).

The bisphenol epoxy resins available commercially from Dai Nippon and noted above are promoted as liquid undiluted epichlorohydrin-bisphenol F epoxy resins having much lower viscosities than conventional epoxy resins based on bisphenol A epoxy resins and have physical properties similar to liquid bisphenol A epoxy resins. Bisphenol F epoxy resin has lower viscosity than bisphenol A epoxy resins, all else being the same between the two types of epoxy resins, which affords a lower viscosity and thus a fast flow underfill sealant material.

The bisphenol epoxy resins available commercially from Resolution and noted above are promoted as low chloride containing liquid epoxy resins. The bisphenol A epoxy resins have a EEW (g/eq) of between 180 and 195 and a viscosity at 25° C. of between 100 and 250 cps. The total chloride content for YL-979 is reported as between 500 and 700 ppm, and that for YL-980 as between 100 and 300 ppm. The total chloride content for RSL-1738 is reported as between 500 and 700 ppm, and that for YL-983U as between 150 and 350 ppm.

In addition to the bisphenol epoxy resins, other epoxy compounds are included within the curable resin component. For instance, cycloaliphatic epoxy resins, such as 3,4-epoxycyclohexylmethyl-3,4-epoxycyclohexylcarbonate, may be used. Also monofunctional, difunctional or multifunctional reactive diluents to adjust the viscosity and/or lower the Tg may also be used, examples of which include butyl glycidyl ether, cresyl glycidyl ether, polyethylene glycol glycidyl ether or polypropylene glycol glycidyl ether.

Among the epoxy resins suitable for use herein also include polyglycidyl derivatives of phenolic compounds, such as those available commercially under the tradename EPON, such as EPON 828, EPON 1001, EPON 1009, and EPON 1031 from Resolution; DER 331, DER 332, DER 334, and DER 542 from Dow Chemical Co.; and BREN-S from Nippon Kayaku. Other suitable epoxy resins include polyepoxides prepared from polyols and the like and polyglycidyl derivatives of phenol-formaldehyde novolacs, the latter of such as DEN 431, DEN 438, and DEN 439 from Dow Chemical. Cresol analogs are also available commercially under the tradename ARALDITE, such as ARALDITE ECN 1235, ARALDITE ECN 1273, and ARALDITE ECN 1299 from Ciba Specialty Chemicals Corporation. SU-8 is a bisphenol-A-type epoxy novolac available from Resolution. Polyglycidyl adducts of amines, aminoalcohols and polycarboxylic acids are also useful in this invention, commercially available resins of which include GLYAMINE 135, GLYAMINE 125, and GLYAMINE 115 from F.I.C. Corporation; ARALDITE MY-720, ARALDITE 0500, and ARALDITE 0510 from Ciba Specialty Chemicals and PGA-X and PGA-C from the Sherwin-Williams Co.

Appropriate monofunctional epoxy coreactant diluents for use herein include those that have a viscosity which is lower than that of the epoxy resin component, ordinarily, less than about 250 cps.

The monofunctional epoxy coreactant diluents should have an epoxy group with an alkyl group of about 6 to about 28 carbon atoms, examples of which include $C_{6-28}$ alkyl glycidyl ethers, $C_{6-28}$ fatty acid glycidyl esters and $C_{6-28}$ alkylphenol glycidyl ethers.

In the event such a monofunctional epoxy coreactant diluent is included, the coreactant diluent should be employed in an amount of up to about 5 percent by weight to about 15 percent by weight, such as about 8 percent by weight to about 12 percent by weight, based on the total weight of the composition.

In addition to compounds and resins having epoxy functionality, compounds and resins having one or more of the following functional groups may be used: episulfide, oxetane, thioxetane, oxazine (such as benzoxazine), oxazoline, maleimide, itaconamide, nadimide, cyanate ester, (meth) acrylate, and combinations thereof.

Compounds and resins having episulfide functionality may be sulfurized versions of any of the epoxy resins. The oxetanes may be 4 membered oxygen-containing ring versions of any of the epoxy resins and the thioxetanes sulfurized versions thereof.

Oxazines, such as benzoxazines, may be embraced by

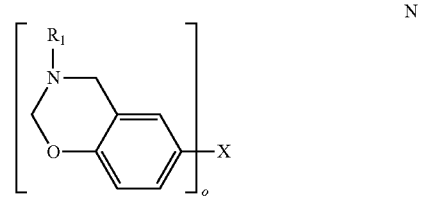

where o is 1-4, X is selected from a direct bond (when o is 2), alkyl (when o is 1), alkylene (when o is 2-4), carbonyl (when o is 2), thiol (when o is 1), thioether (when o is 2), sulfoxide (when o is 2), or sulfone (when o is 2), and $R_1$ is aryl, or

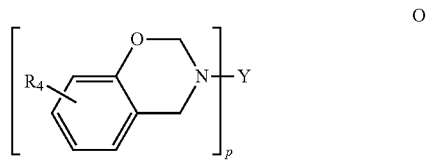

where p is 2, Y is selected from biphenyl (when p is 2), diphenyl methane (when p is 2), diphenyl isopropane (when p is 2), diphenyl sulfide (when p is 2), diphenyl sulfoxide (when p is 2), diphenyl sulfone (when p is 2), or diphenyl ketone (when p is 2), and $R_4$ is selected from hydrogen, halogen, alkyl or alkenyl.

The cyanate esters may be chosen from aryl compounds having at least one cyanate ester group on each molecule and may be generally represented by the formula $Ar(OCN)_m$, where m is an integer from 2 to 5 and Ar is an aromatic radical. The aromatic radical Ar should contain at least 6 carbon atoms, and may be derived, for example, from aromatic hydrocarbons, such as benzene, biphenyl, naphthalene, anthracene, pyrene or the like. The aromatic radical Ar may also be derived from a polynuclear aromatic hydrocarbon in which at least two aromatic rings are attached to each other through a bridging group. Also included are aromatic radicals derived from novolac-type phenolic resins—i.e., cyanate esters of these phenolic resins. The aromatic radical Ar may also contain further ring-attached, non-reactive substituents.

Examples of such cyanate esters include, for instance, 1,3-dicyanatobenzene; 1,4-dicyanatobenzene; 1,3,5-tricyanatobenzene; 1,3-, 1,4-, 1,6-, 1,8-, 2,6- or 2,7-dicyanatonaphthalene; 1,3,6-tricyanatonaphthalene; 4,4'-dicyanatobiphenyl; bis(4-cyanatophenyl)methane and 3,3',5,5'- tetramethyl bis(4-cyanatophenyl)methane; 2,2-bis(3,5-dichloro-4-cyanatophenyl)propane; 2,2-bis(3,5-dibromo-4-dicyanatophenyl)propane; bis(4-cyanatophenyl)ether; bis(4-cyanatophenyl)sulfide; 2,2-bis(4-cyanatophenyl)propane; tris(4-cyanatophenyl)-phosphite; tris(4-cyanatophenyl) phosphate; bis(3-chloro-4-cyanatophenyl)methane; cyanated novolac; 1,3-bis[4-cyanatophenyl-1-(methylethylidene)]benzene and cyanated bisphenol-terminated polycarbonate or other thermoplastic oligomer.

Compounds and resins having (meth)acrylate functionality may be chosen from a host of materials, such as those represented by $H_2C=CGCO_2R^1$, where G may be hydrogen, halogen or alkyl groups having from 1 to about 4 carbon atoms, and $R^1$ may be selected from alkyl, cycloalkyl, alkenyl, cycloalkenyl, alkaryl, aralkyl or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone and the like.

Additional (meth)acrylate(s) suitable for use herein include polyfunctional (meth)acrylate monomers, such as di- or tri-functional (meth)acrylates like polyethylene glycol di(meth)acrylates, tetrahydrofuran (meth)acrylates and di(meth)acrylates, hydroxypropyl (meth)acrylate ("HPMA"), hexanediol di(meth)acrylate, trimethylol propane tri(meth)acrylate ("TMPTMA"), diethylene glycol dimethacrylate, triethylene glycol dimethacrylate ("TRIEGMA"), tetraethylene glycol dimethacrylate, dipropylene glycol dimethacrylate, di-(pentamethylene glycol) dimethacrylate, tetraethylene diglycol diacrylate, diglycerol tetramethacrylate, tetramethylene dimethacrylate, ethylene dimethacrylate, neopentyl glycol diacrylate, trimethylol propane triacrylate and bisphenol-A mono and di(meth)acrylates, such as ethoxylated bisphenol-A (meth)acrylate ("EBIPMA"), and bisphenol-F mono and di(meth)acrylates, such as ethoxylated bisphenol-F (meth)acrylate.

In addition, polyacrylates having (meth)acrylate functionality may also be used. Particularly desirable ones are those prepared through controlled reduced polymerization techniques, such as single electron transfer living radical polymerization techniques. See U.S. Pat. No. 5,807,937 (Matyjaszawski), U.S. Patent Application Publication No. 2010/0331493 (Percec) and U.S. Patent Application Publication No. 2011/0060157 (Glaser).

Still other (meth)acrylates that may be used herein include silicone (meth)acrylate moieties ("SiMA"), such as those taught by and claimed in U.S. Pat. No. 5,605,999 (Chu), the disclosure of which is hereby expressly incorporated herein by reference.

Of course, combinations of these (meth)acrylate(s) may also be used.

The curable resin component should be present in the composition in an amount which the range of about 10 percent by weight to about 95 percent by weight, desirably about 20 percent by weight to about 80 percent by weight, such as about 40 percent by weight to about 65 percent by weight.

As a curative for epoxy resins, imidizoles, dicyandimide, carboxylic acids, anhydrides, phenolic hardeners, amines, thiols, alcohols and alkalines may be used.

The imidazoles include imidazole and derivatives thereof, such as isoimidazole, imidazole, alkyl substituted imidazoles, such as 2-methyl imidazole, 2-ethyl-4-methylimidazole, 2,4-dimethylimidazole, butylimidazole, 2-heptadecenyl-4-methylimidazole, 2-methylimidazole, 2-undecenylimidazole, 1-vinyl-2-methylimidazole, 2-n-heptadecylimidazole, 2-undecylimidazole, 2-heptadecylimidazole, 2-phenylimidazole, 2-ethyl 4-methylimidazole, 1-benzyl-2-methylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole and addition products of an imidazole methylimidazole and addition products of an imidazole and trimellitic acid, 2-n-heptadecyl-4-methylimidazole and the like, generally where each alkyl substituent contains up to about 17 carbon atoms and desirably up to about 6 carbon atoms; aryl substituted imidazoles, such as phenylimidazole, benzylimidazole, 2-methyl-4,5-diphenylimidazole, 2,3,5-triphenylimidazole, 2-styrylimidazole, 1-(dodecyl benzyl)-2-methylimidazole, 2-(2-hydroxyl-4-t-butylphenyl)-4,5-diphenylimidazole, 2-(2-methoxyphenyl)-4,5-diphenylimidazole, 2-(3-hydroxyphenyl)-4-,5-diphenylimidazole, 2-(p-dimethylaminophenyl)-4,5-diphenylimidazole, 2-(2-hydroxyphenyl)-4,5-diphenylimidazole, di(4,5-diphenyl-2-imidazole)-benzene-1,4,2-naphthyl-4,5-diphenylimidazole, 1-benzyl-2-methylimidazole, 2-p-methoxystyrylimidazole, and the like generally where each aryl substituent contains up to about 10 carbon atoms and desirably up to about 8 carbon atoms.

As a curative for free radical curing systems, peroxides are a suitable choice. For instance, hydroperoxides, such as cumene hydroperoxide ("CHP"), para-menthane hydroperoxide, t-butyl hydroperoxide ("TBH") and t-butyl perbenzoate, may be used. Other useful peroxides include benzoyl peroxide, dibenzoyl peroxide, 1,3-bis(t-butylperoxyisopropyl)benzene, diacetyl peroxide, butyl 4,4-bis(t-butylperoxy) valerate, p-chlorobenzoyl peroxide, t-butyl cumyl peroxide, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane and combinations thereof.

The curative should be present in an amount with the range of about 0.05 percent by weight to about 10 percent by weight, desirably about 0.1 percent by weight to about 5 percent by weight, such as about 1 percent by weight of the total composition.

An inorganic filler component may also be used, and include reinforcing silicas, such as fused silicas, and may be untreated or treated so as to alter the chemical nature of their surface. The inorganic filler component however includes particles having a mean particle size distribution in the 1-1,000 nanometer ("nm") range. A commercially available example of such filler particles is sold under the tradename NANOPDX, such as NANOPDX XP 22, by Hans Chemie, Germany. NANOPDX fillers are monodisperse silica filler dispersions in epoxy resins, at a level of up to about 50 percent by weight. NANOPDX fillers ordinarily are believed to have a particle size of about 5 nm to about 80 nm. And NANOPDX XP 22 is reported to contain 40 weight percent of silica particles having a particle size of about 15 nm in the diglycidyl ether of bisphenol-F epoxy resin.

Hans Chemie also produces materials under the NANOPDX E trade designations. For instance, reports Hans Chemie NANOPDX E-brand products enable the complete impregnation of electronic components which are difficult to seal otherwise and provide a large spectrum of mechanical and thermal properties such as reduced shrinkage and thermal expansion, fracture toughness and modulus. In Table A below, Hans Chemie provides information on the four noted NANOPDX E products:

TABLE A

| Type | SiO$_2$-Content [wt %] | Base resin | EEW [g/eq.] | Dyn. viscosity, 25° C. [mPa·s] | Characterization |
|---|---|---|---|---|---|
| NANOPOX E 430 | 40 | DGEBA/DGEBF | 290 | 45,000 | no crystallization |
| NANOPOX E 470 | 40 | DGEBA | 295 | 60,000 | basic type |
| NANOPOX E 500 | 40 | DGEBF | 275 | 20,000 | low viscous |
| NANOPOX E 600 | 40 | EEC[1] | 220 | 4,000 | cycloaliphatic formulations |

[1]3,4-epoxycyclohexylmethyl-3,4-epoxycyclohexylcarbonate

Hans Chemie reports that important properties can be significantly improved in epoxy formulations by using NANOPDX E-brand products. For instance:

lower viscosity of the formulation in comparison to conventional reinforced fillers no sedimentation increase in the fracture toughness, impact resistance and modulus improved scratch and abrasion resistance reduction of shrinkage and thermal expansion improvement, or at least no negative effect, in numerous desired properties, such as: thermal stability, chemical resistance, glass transition temperature, weathering resistance, dielectric properties.

The combination of NANOPDX E with conventional fillers—such as quartz—enables a reduction in the resin content of the formulation, which means that the total filler content can be increased to previously unattained levels.

The processability remains essentially unchanged in comparison to the respective base resin.

NANOPDX E is used in applications where the above improvements to properties desired or necessary, without compromising the processability by an excessive increase in viscosity (known from fumed silica). Application examples are encapsulation materials and coatings. It is important to emphasize the excellent impregnation properties of NANOPDX E due to the small particle size and the absence of agglomerates. This also enables the complete impregnation of electronic components which are difficult to seal otherwise.

According to the manufacturer, NANOPDX E-brand products are a colloidal silica sol in an epoxy resin matrix. The disperse phase consists of surface-modified, spherically shaped SiO$_2$ nanoparticles with diameters below 50 nm and an extremely narrow particle size distribution. These spheres, only a few nanometers in size, are distributed agglomerate-free in the resin matrix. This produces a very low viscosity of the dispersion with SiO$_2$ content of up to 40 percent by weight. The nanoparticles are chemically synthesized from aqueous sodium silicate solution.

Other desirable materials for use as the inorganic filler component include those constructed of or containing aluminum oxide, silicon nitride, aluminum nitride, silica-coated aluminum nitride, boron nitride and combinations thereof, provided of course particles having a mean particle size distribution in the 1-1,000 nm range.

The inorganic filler component should be used in an amount of about 10 to about 80 percent by weight of the composition, such as about 12 to about 60 percent by weight, desirably within the range of about 15 to about 35 percent by weight.

In addition, adhesion promoters, such as the silanes, glycidyl trimethoxysilane (commercially available from OSI under the trade designation A-187) or gamma-amino propyl triethoxysilane (commercially available from OSI under the trade designation A-1100), may be used.

Conventional additives may also be used in the compositions of the present invention to achieve certain desired physical properties of the composition, the cured reaction product, or both.

The thermosetting resin compositions are capable of penetrating into the space between the circuit board and the semiconductor device and function in this way as an underfill sealant. These inventive compositions also demonstrate a reduced viscosity, at least under elevated temperature conditions, and thus are capable of penetrating into that space. It is desirable to prepare the thermosetting resin composition by selecting the types and proportions of various ingredients to reach a viscosity at 25° C. of 5,000 mPa·s or less, such as 300 to 2,000 mPa·s, so as to improve its ability to penetrate into the space (e.g., of 10 to 500 μm) between the circuit board and the semiconductor device.

Reference to FIG. 1 shows an example of a subcomponent, such as a CSP, in which the thermosetting resin composition of the present invention is used.

The semiconductor device 4 is formed by connecting a semiconductor chip 2 to a carrier substrate 1 and sealing the space therebetween suitably with resin 3. This semiconductor device is mounted at a predetermined position of the circuit board 5, and electrodes 8 and 9 are electrically connected by a suitable connection means such as solder. In order to improve reliability, the space between carrier substrate 1 and circuit board 5 is sealed with the cured product 10 of a thermosetting resin composition. The cured product 10 of the thermosetting resin composition need not completely fill the space between carrier substrate 1 and circuit board 5, but may fill it to such an extent as to relieve stresses caused by thermal cycling.

Carrier substrates may be constructed from ceramic substrates made of Al$_2$O$_3$, SiN$_3$ and mullite (Al$_2$O$_3$—SiO$_2$); substrates or tapes made of heat-resistant resins such as polyimides; glass-reinforced epoxy, ABS and phenolic substrates which are also used commonly as circuit boards; and the like.

Figure 2:
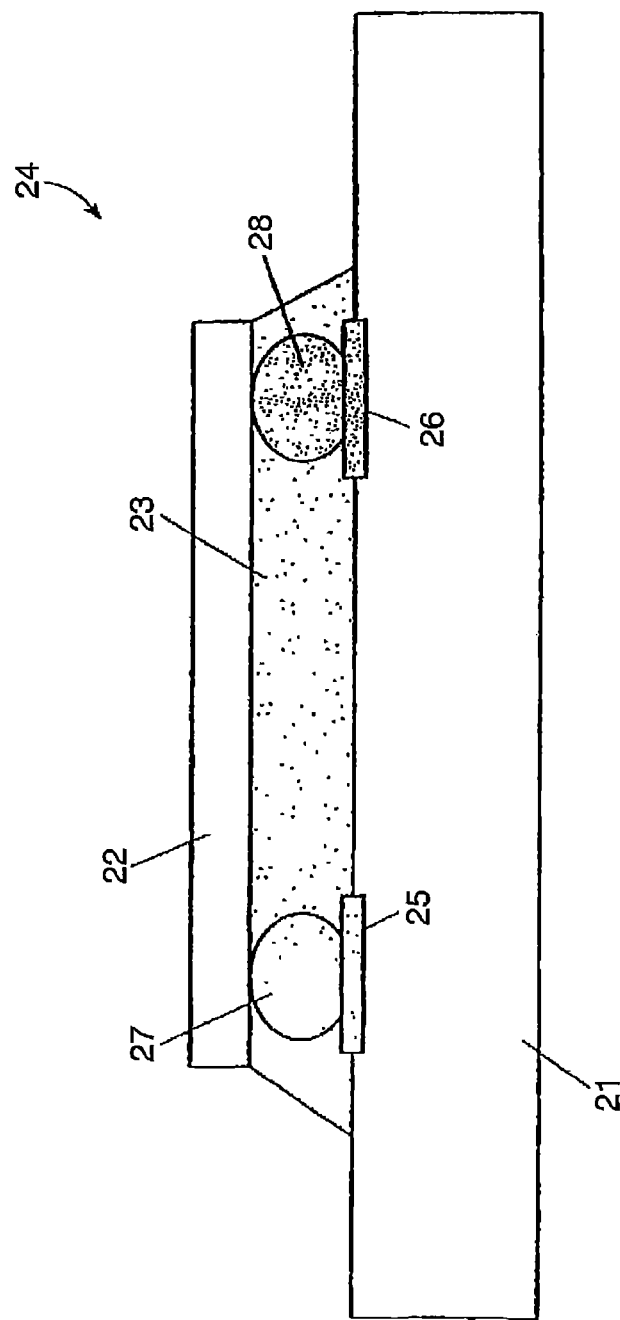
FIG. 2 depicts a cross-sectional view showing an example of a semiconductor flip chip assembly in which the thermosetting resin composition of the present invention is used.

As regards flip chip assemblies, reference to FIG. 2 shows a flip chip assembly in which a semiconductor chip has been mounted onto a circuit board, and the underfilling sealed with a thermosetting resin composition.

The flip chip assembly 24 is formed by connecting a semiconductor chip 22 to a circuit board 21 and sealing the space therebetween suitably with a thermosetting resin composition 23. This semiconductor device is mounted at a predetermined position on the circuit board 21 and electrodes 25 and 26 are electrically connected by a suitable electrical connection means 27 and 28, such as solder. In order to improve reliability, the space between the semiconductor chip 22 and the circuit board 21 is sealed with a thermosetting resin composition 23 and then cured. The cured product of the thermosetting resin composition should completely fill that space.

No particular limitation is placed on the means for electrically connecting the semiconductor chip to the carrier substrate, and there may be employed connection by a high-melting solder or electrically (or anisotropically) conductive adhesive, wire bonding, and the like. In order to facilitate connections, the electrodes may be formed as bumps. Moreover, in order to improve the reliability and durability of connections, the space between the semiconductor chip and the carrier substrate may be sealed with a suitable resin. The semiconductor devices that can be used in the present invention include CSPs, BGAs, and LGAs.

The circuit board may be constructed from common materials, such as glass-reinforced epoxy, ABS, benzoxazine and phenolic resin.

Next, in the mounting process, cream solder is printed at the necessary positions of a circuit board and suitably dried to expel the solvent. Then, a semiconductor device is mounted in conformity with the pattern on the circuit board. This circuit board is passed through a reflowing furnace to melt the solder and thereby solder the semiconductor device. The electrical connection between the semiconductor device and the circuit board is not limited to the use of cream solder, but may be made by use of solder balls. Alternatively, this connection may also be made through an electrically conductive adhesive or an anisotropically conductive adhesive. Moreover, cream solder or the like may be applied or formed on either the circuit board or the semiconductor device. In order to facilitate subsequent repairs, the solder, electrically or anisotropically conductive adhesive used should be chosen bearing in mind its melting point, bond strength and the like.

After the semiconductor device is electrically connected to the circuit board in this manner, the resulting structure should ordinarily be subjected to a continuity test or the like. After passing such test, the semiconductor device may be fixed thereto with a resin composition. In this way, in the event of a failure, it is easier to remove the semiconductor device before fixing it with the resin composition.

Then, a thermosetting resin composition may be applied to the periphery of the semiconductor device. When this composition is applied to the semiconductor device, it penetrates into the space between the circuit board and the carrier substrate of the semiconductor device by capillary action.

The thermosetting resin composition is cured by the application of heat. During the early stage of this heating, the thermosetting resin composition shows a significant reduction in viscosity and hence an increase in fluidity, so that it more easily penetrates into the space between the circuit board and the semiconductor device. Moreover, by providing the circuit board with suitable venting holes, the thermosetting resin composition is allowed to penetrate fully into the entire space between the circuit board and the semiconductor device.

The amount of thermosetting resin composition applied should be adjusted so as to fill the space between the circuit board and the semiconductor device almost completely.

The thermosetting resin composition ordinarily should be cured by heating at a temperature of about 100° C. to about 150° C. for a period of time of about 5 to about 60 minutes, such as about 110° C. to about 130° C. for a period of time of about 15 to about 45 minutes. Thus, relatively low-temperature and short-time curing conditions may be employed to achieve very good productivity. The subcomponent illustrated in FIG. 1 may be constructed in this manner. Ordinary epoxy-based compositions used for this purpose, such as those based solely on bisphenol-A-type epoxy resins or bisphenol-F-type epoxy resins as the epoxy resin do not have the same degradation pathway available, and instead only start to decompose at about 300° C.

After the semiconductor device is so mounted on the circuit board, the resulting subcomponent may be tested for operability. In the event a failure is found, repair can be made in the following manner.

The area around the semiconductor device that has failed is heated locally at a temperature of about 170° C. to about 240° C. for a period of time ranging from about 10 seconds to about 60 seconds, such as a temperature of about 220° C. for a period of time of 30 seconds.

As soon as the solder is melted and the resin is softened to cause a reduction in bond strength, the semiconductor device is pulled apart.

After the semiconductor device is removed, a residue of the cured reaction product of the thermosetting resin composition and a residue of the solder are left on the circuit board. The residue of the cured reaction product of the thermosetting resin composition can be removed, for example, simply by wiping the device with a low abrasive cloth. (See FIG. 3.) In the past, processed reaction products would have to be scraped off after the residue has been softened by heating it to a predetermined temperature, allowing it to swell with solvent, or allowing it to swell with solvent while heating it to a predetermined temperature. (See FIG. 3.)

Finally, on the circuit board which has been cleaned, a new semiconductor device may be mounted again in the same manner as described previously. Thus, the repair of the failure site is completed.

Where a failure is found in the circuit board, the semiconductor device can be reused if desired by removing the residue of the cured reaction product of the thermosetting resin composition and the residue of the solder left on the bottom of the semiconductor device in the same manner as described above.

While the inventive compositions have been described as being useful primarily as an underfill sealant, it is also contemplated that the inventive compositions may be used in liquid compression molding applications, as structural adhesives, such as in the construction of hand held display devices, like smart phones and tablets, films for semiconductor packaging, short/long term encapsulants for passive electronic components, and coatings.

The invention will be further illustrated by the following non-limiting examples.

EXAMPLES

Synthesis

Example 1

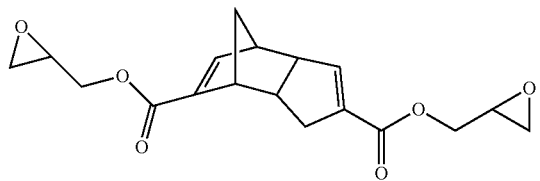 [SMILES: O=C(OCC1CO1)C1=CC2C3C=C(C(=O)OCC4CO4)C(C3)C2C1]

In a 1 L 4 necked flask equipped with a mechanical stirrer and addition funnel was placed the dicarboxylic acid of DCPD ("DCPD diacid") (50 g, 227 mmol) together with DMSO (300 mL). KOH (26.8 g) in 30 mL of water was added slowly over a period of 5 minutes, and stirred continuously for an additional period of 15 minutes. The reaction mixture was then heated using an oil bath at a temperature of 50° C. Epibromohydrin (124.4 g, 908 mmol) in 25 mL of DMSO was added dropwise over a period of 2 hours, and stirred continuously for an additional 6 hours.

The reaction mixture was extracted with 600 mL of ethyl acetate, washed with aqueous NaHCO$_3$ solution, washed several times with water and then dried over anhydrous MgSO$_4$. The solvent was evaporated to afford a brown liquid, which was then diluted with 50 mL of toluene and distilled to afford the diglycidyl ester of DCPD diacid ("DCPD epoxy") (60 g, 80% yield).

Example 2

DCPD epoxy (2.06 g, 6.2 mmol), methacrylic acid (0.54 g, 6.2 mmol), tetrabutylammonium iodide (100 mg) and t-butylcatechol (30 mg) were placed in a round bottom flask, together with THF (20 mL), and mixed at reflux for a period of 5 hours. After cooling the reaction mixture to room temperature, ethyl acetate was added and the organic layer was washed twice with saturated aqueous NaHCO$_3$, washed with aqueous K$_2$CO$_3$ and dried over anhydrous MgSO$_4$. The solvent was then evaporated to afford DCPD hybrid epoxy-methacrylate as a viscous dark brown liquid (1.82 g, 70% yield).

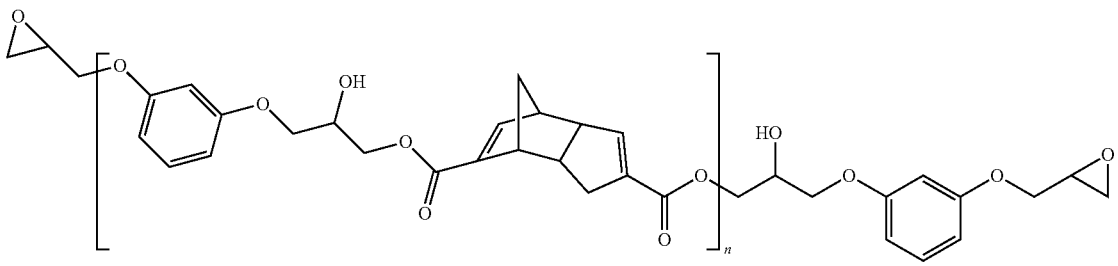

In a 1 L 4 necked flask equipped with a nitrogen inlet and mechanical stirrer was placed the DCPD diacid (15.2 g, 69 mmol) and resorcinol diglycidyl ether (30.7 g, 138 mmol) in THF (450 mL). After stirring for a period of 30 minutes, a catalytic amount of tetrabutylammonium iodide (1.27 g, 3.44 mmol) was added and the mixture was heated to reflux for a period of 36 hours. An infrared ("IR") spectral analysis was performed, the results of which indicated the appearance of a carbonyl band at 1707 cm$^{-1}$ distinct from the DCPD diacid.

After cooling the reaction mixture to room temperature, the THF was evaporated and 600 mL of ethyl acetate was added to the residue. The organic layer was washed several times with water, washed with saturated aqueous NaHCO$_3$, and then washed with water again. After drying over anhydrous MgSO$_4$, the solvent was evaporated to afford the DCPD chain extended epoxy shown above as a dark brown viscous liquid (35 g, 78% yield).

IR spectral analysis of the DCPD chain extended epoxy showed a carbonyl band at 1707 cm$^{-1}$.

Example 3

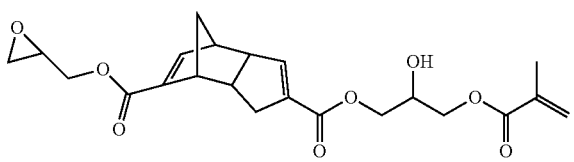 [SMILES: C=C(C)C(=O)OCC(O)COC(=O)C1=CC2C3C=C(C(=O)OCC4CO4)C(C3)C2C1]

Example 4

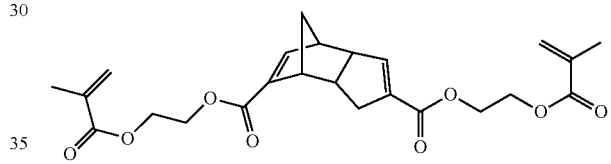

In a 500 mL 4 necked flask equipped with a nitrogen inlet was placed DCPD diacid (35.7 g, 162 mmol) in THF (300 mL). The mixture was cooled with an ice-salt bath and oxalyl chloride (61.7 g, 486 mmol) was added dropwise over a period of 5 minutes. The reaction mixture was allowed to reach room temperature and stirred for an additional 4 hours. The solvent and excess oxalyl chloride were evaporated, the residue was dissolved in THF (200 mL) under nitrogen atmosphere, and the solution cooled with ice. Triethylamine (41 g, 405 mmol) was added with stirring, followed by HEMA (42.2 g, 324 mmol) over a period of 30 minutes and t-butylcatechol (140 mg) was added with stirring. After about 4 h, THF was evaporated and the reaction mixture was extracted with ethyl acetate (400 mL), washed with water 4 times and dried over anhydrous MgSO$_4$. The solvent was evaporated to afford the DCPD dimethacrylate as a dark brown liquid (57 g, 73% yield), which was purified by column chromatography.

Example 5

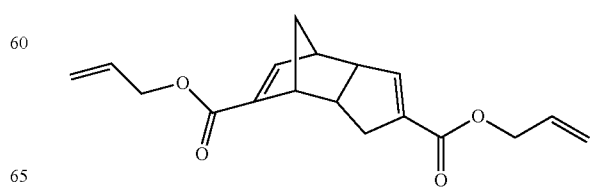

DCPD diacid (29 g, 132 mmol) was dissolved in DMF, and K$_2$CO$_3$ (36 g, 263 mmol) was added with stirring for 30 minutes. Allyl bromide (42 g, 347 mmol) was then added portion wise over a period of 10 minutes. The reaction mixture was stirred at room temperature overnight. The reaction mixture was later extracted with ethyl acetate (500 ml), washed with water 4 times and dried over anhydrous MgSO$_4$. The solvent was evaporated to afford the diallyl ester of DCPD diacid (31 g, 78% yield).

Example 6

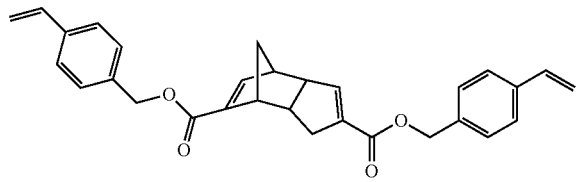 [SMILES: C=Cc1ccc(COC(=O)C2=CC3C4C=C(C(=O)OCc5ccc(C=C)cc5)C(C4)C3C2)cc1]

In a 250 mL flask with a magnetic stirring bar was placed DCPD diacid (4.5 g, 20.4 mmol), DMSO (100 mL), and K$_2$O$_3$ (3.39 g, 24.5 mmol) with stirring for a period of time of 15 minutes. 4-Vinylbenzyl chloride (7.2 g, 47.2 mmol) was added and the reaction mixture stirred at room temperature overnight.

IR spectral analysis showed a carbonyl band at 1709 cm$^{-1}$ for the ester.

The reaction mixture was extracted with ethyl acetate, washed with water several times and dried over anhydrous MgSO$_4$. The solvent was evaporated and the reaction mixture was purified by column chromatography to afford the distyrenic derivative of DCPD diacid as a yellow oil (5.3 g, 58% yield).

Example 7

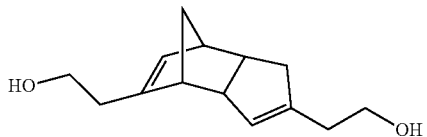 [SMILES: OCCC1=CC2C3CC(C=C3CCO)C2C1]

In a 3 necked 250 mL flask equipped with a nitrogen inlet and magnetic stirring bar was placed a 2M solution of sodium cyclopentadienylide in THF (30 ml, 60 mmol) in THF (50 mL). The suspension was cooled in ice for a period of time of about 30 minutes, after which a solution of (2-bromoethoxy)-tert-butyldimethylsilane (14.34 g, 60 mmol) was added dropwise over a period of time of about 30 minutes. The mixture was allowed to stir at the same temperature for a period of time of about 2 hours, and then at room temperature overnight. THF was evaporated and the product extracted with ethyl acetate (200 ml), washed with water, and dried over anhydrous MgSO$_4$. The solvent was evaporated to give the intermediate crude silyl derivative of 2-hydroxyethyl cyclopentadiene, which was dimerized by heating at a temperature of about 110° C. for a period of time of about 1.5 hours to provide the silyl derivative of intermediate DCPD diethanol.

To a solution of this crude product in THF (50 mL) was added a 1M solution of TBAF in THF (60 mL, 60 mmol) and the mixture stirred at room temperature overnight. THF was evaporated and the product extracted with ethyl acetate (200 ml), washed with water and dried over anhydrous MgSO$_4$. Solvent evaporation provided DCPD diethanol as a brown oil (8.1 g, 61% yield).

Example 8

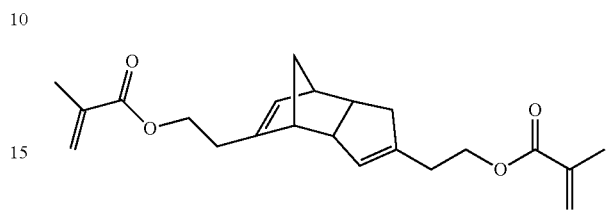

In a 3 necked 100 mL flask equipped with a nitrogen inlet and a magnetic stirring bar was placed bishydroxyethyl DCPD (1.05 g, 4.8 mmol) in CH$_2$Cl$_2$ (25 mL). Triethylamine (2.41 g, 23.8 mmol) and a catalytic amount of DMAP (50 mg) were added. The resulting mixture was cooled with ice and methacrylic anhydride (2.94 g, 19.1 mmol) added dropwise. After stirring at the same temperature for a period of time of about 30 minutes and then at room temperature for an additional period of time of about 3 hours, aqueous NaHCO$_3$ solution (30 mL) was added. CH$_2$Cl$_2$ was then evaporated and the product extracted with ethyl acetate. The organic layer was washed with water and dried over anhydrous MgSO$_4$. t-Butylcatechol (200 ppm) was added and the solvent evaporated to provide the dimethacrylate ester of DCPD diethanol (1.4 g, 82% yield).

Example 9

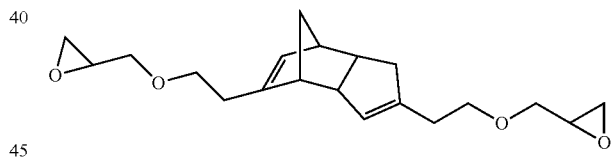

In a 3 necked 100 mL flask equipped with a nitrogen inlet and magnetic stirring bar was added NaH (2.18 g, 60% dispersion in oil, 54.4 mmol) in dry DMF (25 mL). The solution was cooled in an ice bath and a solution of bishydroxyethyl DCPD (3 g, 13.6 mmol) in dry DMF (25 mL) was added slowly over a period of time of about 15 minutes. After stirring for an additional period of time of about 30 minutes, epibromohydrin (7.47 g, 54.4 mmol) was added slowly dropwise. The mixture was warmed to room temperature and allowed to stir overnight, after which isopropanol was added, followed by toluene (200 ml). The organic layer was washed several times with water, and dried over anhydrous MgSO$_4$, before evaporating the solvent. The crude reaction product was purified by column chromatography to isolate the diglycidyl ether (2.3 g, 51% yield).

Thermosetting Resin Compositions

Thermosetting resin compositions may be prepared from the components as noted below in Table 1, with each sample containing less than 1 percent by weight of an air release agent, and a silane adhesion promoter.

TABLE 1

| Type | Identity | A | B | C | D |
|---|---|---|---|---|---|
| Epoxy | Bisphenol A epichlorohydrin copolymer[1] | 30.80 | 30.80 | 30.80 | 30.80 |
| | Bisphenol A, Phenol, formaldehyde, epichlorohydrin copolymer[2] | 31.20 | 29.20 | 26.20 | 21.20 |
| | DCPD Epoxy[3] | — | 2.00 | 5.00 | 10.00 |
| | Epoxy reactive diluent[4] | 15.40 | 15.40 | 15.40 | 15.40 |
| Curative | DYHARD 100-S[5] | 3.60 | 3.60 | 3.60 | 3.60 |
| | NOVACURE HXA3932HP[6] | 16.70 | 16.70 | 16.70 | 16.70 |

[1]EPOTOHTO YD-8125, commercially available from Tohto Kasei
[2]EPOTOHTO ZX-1059, commercially available from Tohto Kasei
[3]Compound A
[4]DENACOL EX-146, para-tertiary butylphenyl glycidyl ether, commercially available from Nagase Chemtex Corporation
[5]commercially available from AlzChem LLC
[6]commercially available from Asahi Kasei Chemicals Corporation

TABLE 2

| Type | Identity | E | F |
|---|---|---|---|
| Epoxy | Epichlorohydrin-formaldehyde-phenol polymer[4] | 15.00 | 10.00 |
| | 2,6-diglycidylphenyl glycidyl ether | 5.00 | 5.00 |
| | Difunctional epoxy[5] | 25.00 | 20.00 |
| | DCPD Epoxy | — | 10.00 |
| | Epoxy reactive diluent[4] | 6.00 | 6.00 |
| Acrylate | Difunctional Acrylate[1] | 9.90 | 9.90 |
| | Monofunctional Methacrylate[2] | 5.00 | 5.00 |
| Curative | NOVACURE HXA3932HP | 13.00 | 13.00 |
| Radical Initiator/Inhibitor | Radical Initiator[3] | 0.60 | 0.60 |
| | Inhibitor | 0.10 | 0.10 |
| Crosslinker | Epoxy acrylate crosslinker | 8.00 | 8.00 |

[1]SR833-S, tricyclodecane dimethanol diacrylate, commercially available from Sartomer, Inc.
[2]SR423-A, isobornyl methacrylate, commercially available from Sartomer, Inc.
[3]TRIGONOX 21s, tertiary-butyl peroxy-2-ethylhexanoate, commercially available from Akzo Nobel Polymer Chemicals LLC
[4]EPICLON 830-CRP, bisphenol F, commercially available from Dainippon Ink and Chemicals, Inc.
[5]EPICLON HP-4032D, 1,6-bis(2,3-epoxypropoxy)naphthalene, commercially available from Dainippon Ink and Chemicals Inc.

TABLE 3

| Type | Identity | G | H | I | J |
|---|---|---|---|---|---|
| Epoxy | Bisphenol A epichlorohydrin copolymer[1] | 30.80 | 30.80 | 30.80 | 30.80 |
| | Bisphenol A, Phenol, formaldehyde, epichlorohydrin copolymer[2] | 31.20 | 29.20 | 26.20 | 21.20 |
| | Resorcinol DCPD Epoxy[3] | — | 4.00 | 10.00 | 16.00 |
| | Epoxy reactive diluent[4] | 15.40 | 15.40 | 15.40 | 15.40 |
| Curative | CUREZOL2MZ-Azine | 3.60 | 3.60 | 3.60 | 3.60 |
| | NOVACURE HXA3932HP | 16.70 | 16.70 | 16.70 | 16.70 |

[1]EPOTOHTO YD-8125, commercially available from Tohto Kasei
[2]EPOTOHTO ZX-1059, commercially available from Tohto Kasei
[3]Compound H
[4]DENACOL EX-146, para-tertiary butylphenyl glycidyl ether, commercially available from Dainippon Ink and Chemicals, Inc.

TABLE 4

| Type | Identity | K | L | M |
|---|---|---|---|---|
| Epoxy | Bisphenol A epichlorohydrin copolymer[1] | 30.50 | 29.00 | 27.50 |
| | Bisphenol A, Phenol, formaldehyde, epichlorohydrin copolymer[2] | 27.50 | 27.50 | 27.50 |
| | DCPD Epoxy[3] | 2.00 | 3.50 | 5.00 |
| | Epoxy reactive diluent[4] | 17.10 | 17.10 | 17.10 |
| Curative | DYHARD 100-S | 1.90 | 1.90 | 1.90 |
| | CUREZOL 2MZ-Azine | 1.90 | 1.90 | 1.90 |

[1]EPOTOHTO YD-8125, commercially available from Tohto Kasei
[2]EPOTOHTO ZX-1059, commercially available from Tohto Kasei
[3]Compound A
[4]DENACOL EX-146, para-tertiary butylphenyl glycidylether, commercially available from Dainippon Ink and Chemicals, Inc.

HYSOL UF 3808 and HYSOL UF 3800, commercially available from Henkel Electronic Materials, LLC, Irvine, Calif., were used for comparative purposes, and are simply referred to by the product names.

Physical Properties

In the uncured state, each of the samples was dispensed from a syringe or jet-dispenser beside an 6×6 mm wafer-level CSP ("WL-CSP") at a dispensing temperature of about 25° C. The samples flowed by capillary action in less than 30 seconds into underfill space between the WL-CSP and a circuit board to which the samples were attached.

The samples were cured by exposure to elevated temperature conditions in the range of about 100° C. to about 150° C. for a period of time of between about 10 to about sixty (60) minutes.

Reference to Tables 5-7 below shows Dynamic Mechanical Analysis ("DMA") data of the cured compositions, Samples A-K.

TABLE 5

| | Modulus @ (log Mpa) | | | |
|---|---|---|---|---|
| Sample | −75° C. | 25° C. | 220° C. | Tg, tan δ (° C.) |
| A | 2964 | 2353 | 35.63 | 142 |
| B | 2627 | 1987 | 33.68 | 148 |
| C | 2713 | 2092 | 22.41 | 145 |
| D | 2757 | 2159 | 11.58 | 140 |

Figure 4:
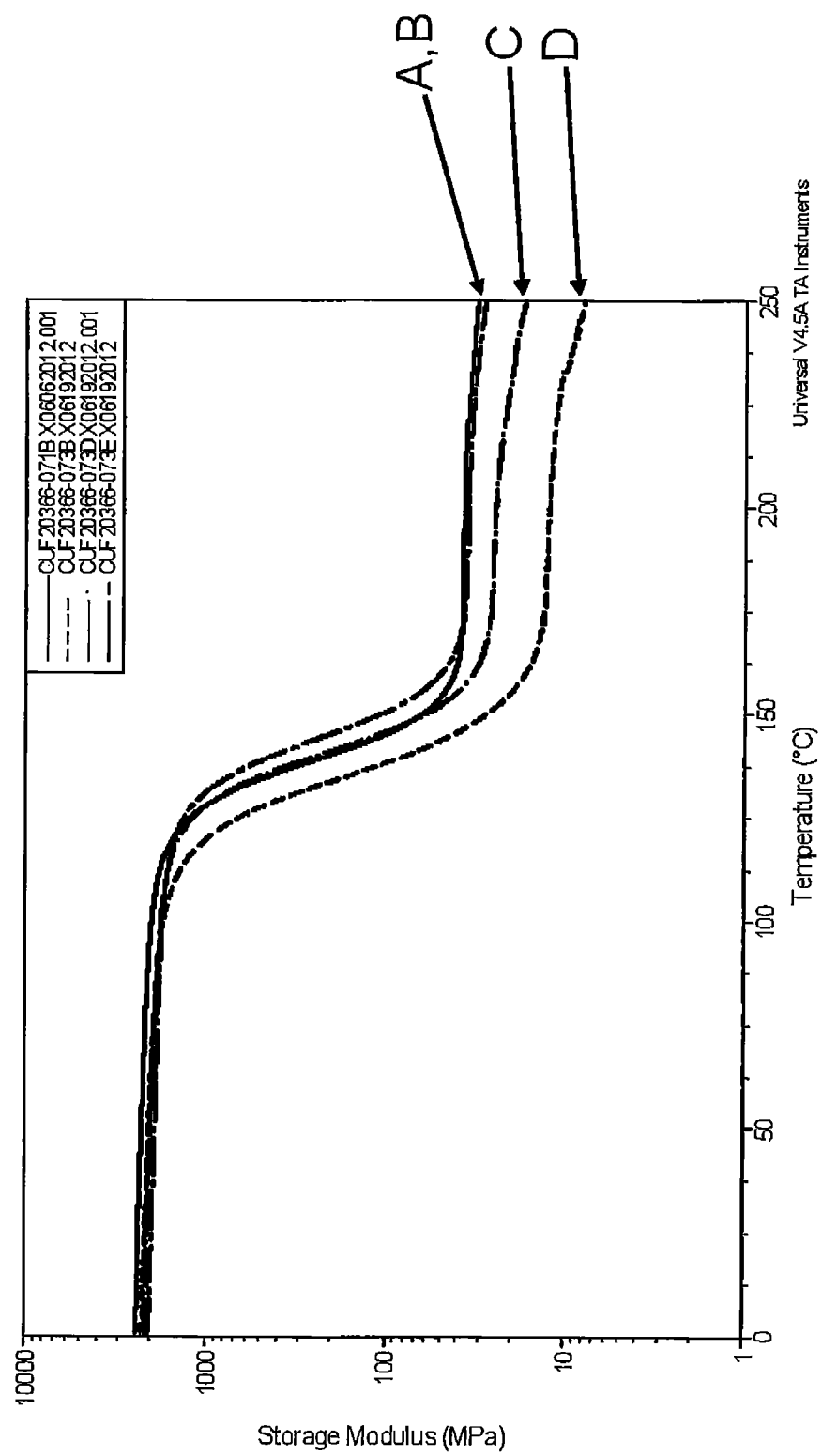
FIG. 4 depicts a trace of storage modulus over temperature for Samples A-D.

FIG. 4 shows modulus over temperature for each of the samples referred to in Table 5.

TABLE 6

| | Modulus @ (log Mpa) | | | |
|---|---|---|---|---|
| Sample | −75° C. | 25° C. | 220° C. | Tg, tan δ (° C.) |
| E | 3597 | 2838 | 125.60 | 144 |
| F | 3241 | 2508 | 40.59 | 147 |

Figure 5:
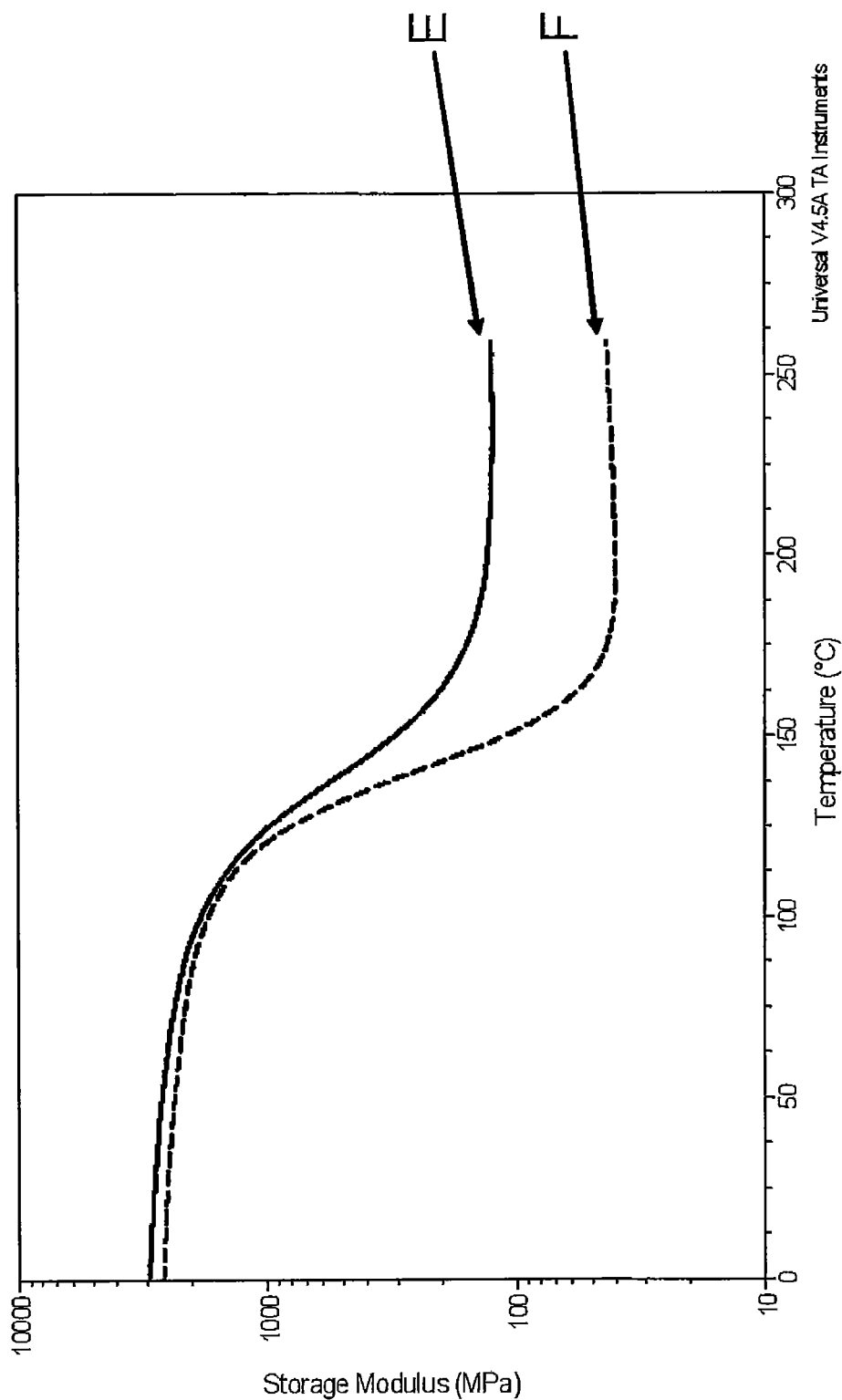
FIG. 5 depicts a trace of storage modulus over temperature for Samples E and F.

FIG. 5 shows modulus over temperature for each of the samples referred to in Table 6.

TABLE 7

| Sample | Modulus @ (log Mpa) | | | Tg, tan δ (° C.) |
|---|---|---|---|---|
| | −75° C. | 25° C. | 220° C. | |
| G | 3057 | 2328 | 79.95 | 145 |
| H | 2447 | 1702 | 70.74 | 141 |
| I | 2697 | 1801 | 63.51 | 142 |
| J | 2381 | 1795 | 44.63 | 138 |

Figure 10:
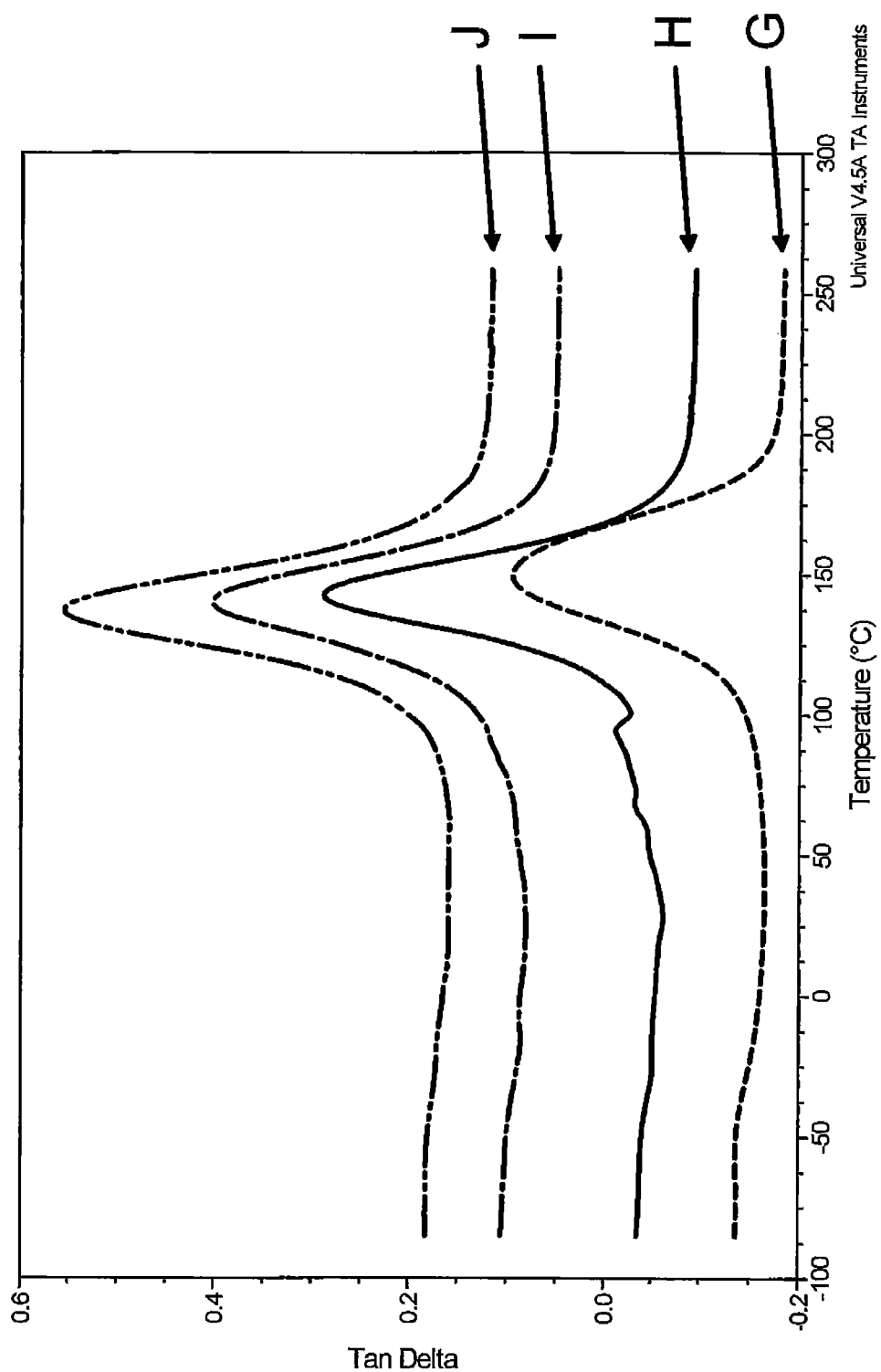
FIG. 10 depicts a trace of tan delta over temperature for each of the samples referred to in Table 7.

FIG. 10 shows tan delta over temperature for each of the samples referred to in Table 7.

Thermal Cycling Tests

Reference to Table 8 below gives the modulus values from the dynamic mechanical analyses of thermal cycling results from four cycles of −85° C. to 250° C. to −85° C. at a ramp rate of 3° C./minute.

TABLE 8

| Sample | Modulus @ (log Mpa) | | | Tg, tan δ (° C.) | Δtan δ Cycle 1/ Cycle 4 | Modulus @ 25° C. Cycle 1/ Cycle 4 |
|---|---|---|---|---|---|---|
| | −75° C. | 25° C. | 220° C. | | | |
| Cycle 1 | | | | | | |
| HYSOL UF 3800 | 3282 | 2561 | 57.20 | 120 | +3 | 721 |
| HYSOL UF 3808 | 3128 | 2595 | 114.15 | 136 | +24 | 880 |
| L | 3220 | 2514 | 48.78 | 143 | −10 | 767 |
| M | 3222 | 2526 | 38.86 | 146 | −13 | 917 |
| N | 3177 | 2509 | 35.20 | 145 | −14 | 968 |
| Cycle 2 | | | | | | |
| HYSOL UF 3800 | 2480 | 1841 | 55.10 | 123 | | |
| HYSOL UF 3808 | 1827 | 1808 | 114.13 | 157 | | |
| L | 1834 | 1834 | 40.78 | 135 | | |
| M | 1701 | 1742 | 30.63 | 134 | | |
| N | 1605 | 1650 | 27.81 | 133 | | |
| Cycle 3 | | | | | | |
| HYSOL UF 3800 | 2480 | 1841 | 54.00 | 123 | | |
| HYSOL UF 3808 | 1766 | 1751 | 114.12 | 159 | | |
| L | 1811 | 1790 | 39.33 | 134 | | |
| M | 1678 | 1650 | 29.24 | 133 | | |
| N | 1581 | 1605 | 26.89 | 132 | | |
| Cycle 4 | | | | | | |
| HYSOL UF 3800 | 2480 | 1840 | 53.50 | 123 | | |
| HYSOL UF 3808 | 1727 | 1715 | 114.11 | 160 | | |
| L | 1756 | 1747 | 38.36 | 133 | | |
| M | 1659 | 1609 | 28.24 | 133 | | |
| N | 1516 | 1541 | 26.18 | 131 | | |

Figure 6:
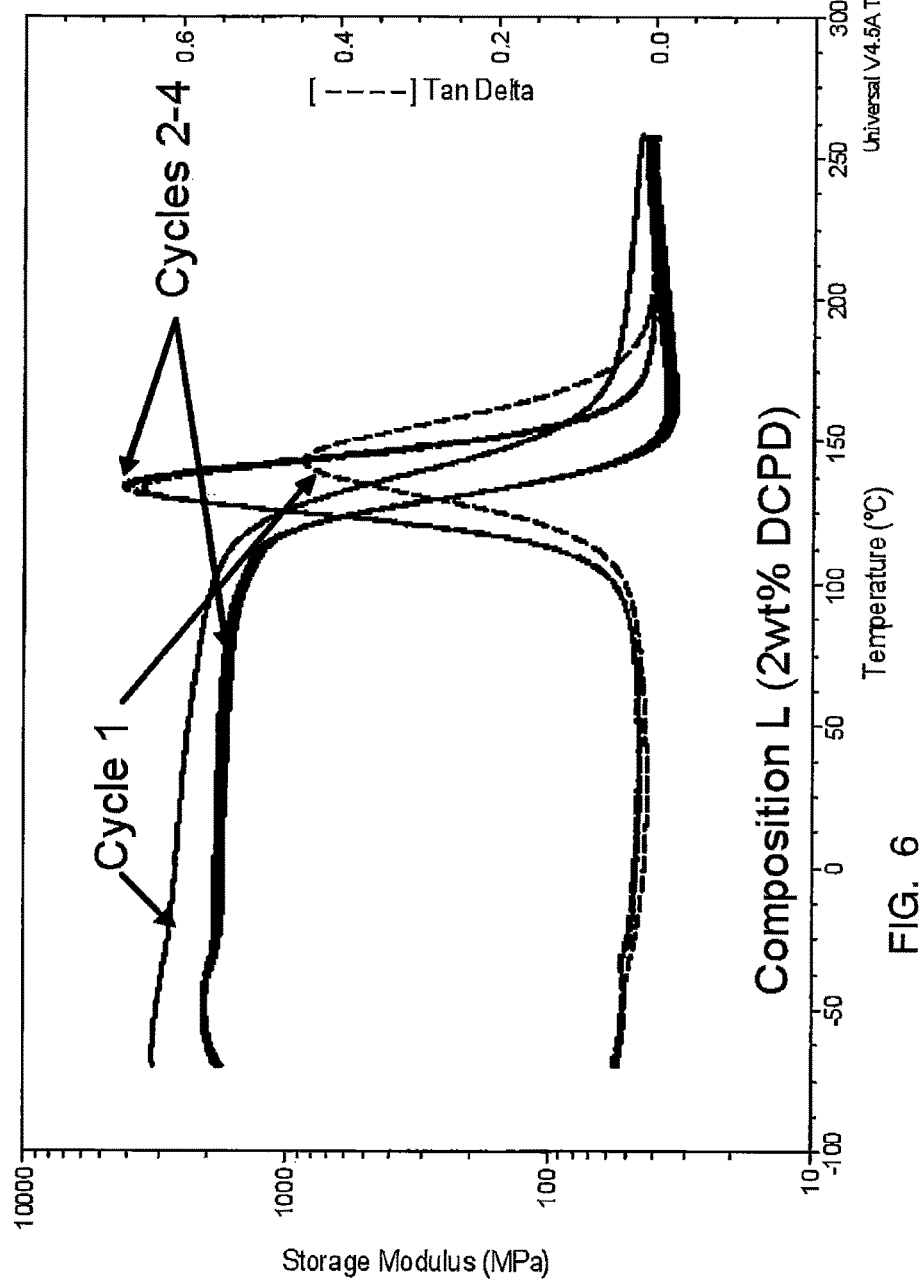
FIG. 6 depicts a trace of storage modulus over temperature for Sample L.
Figure 7:
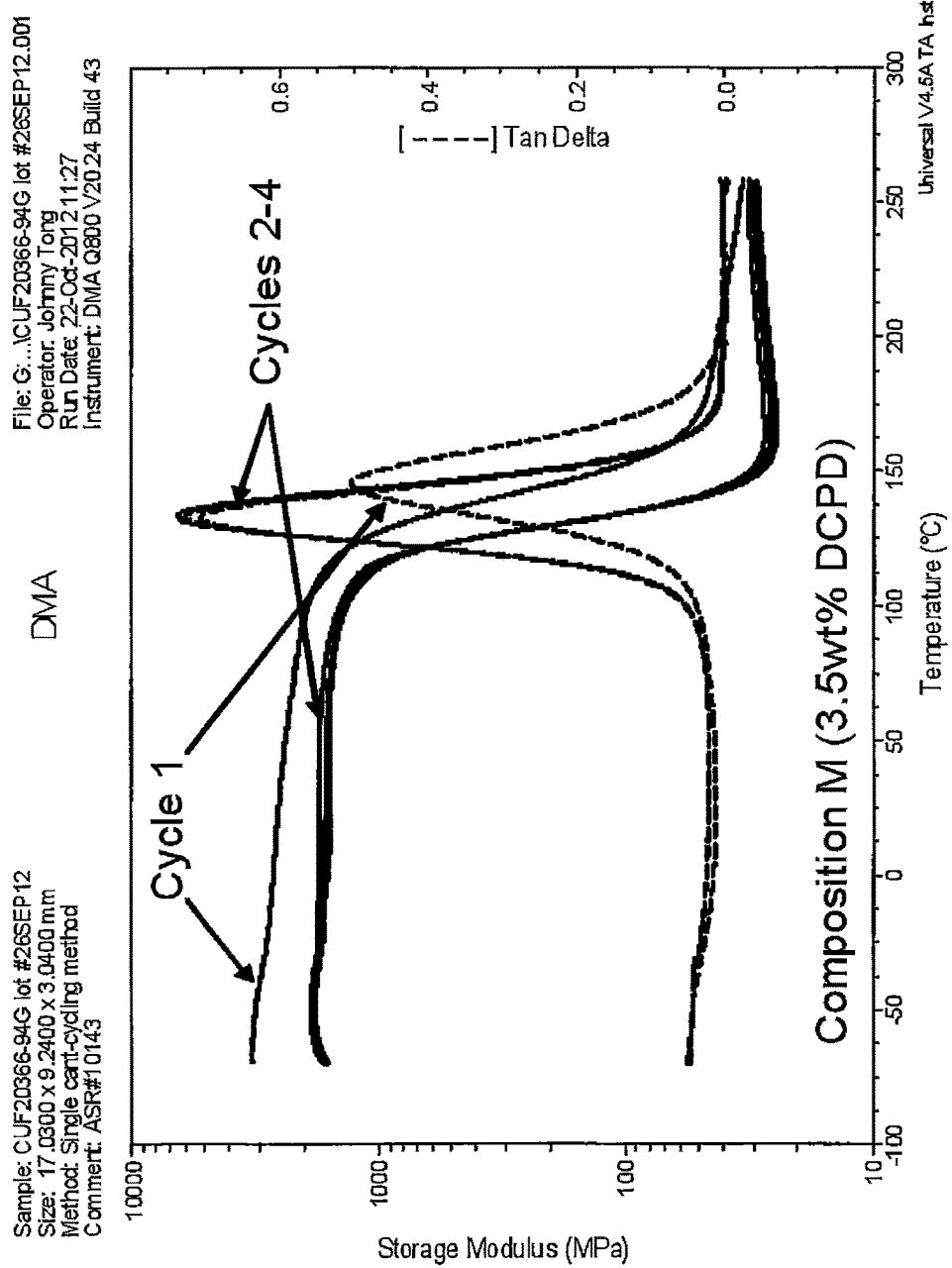
FIG. 7 depicts a trace of storage modulus over temperature for Sample M.
Figure 8:
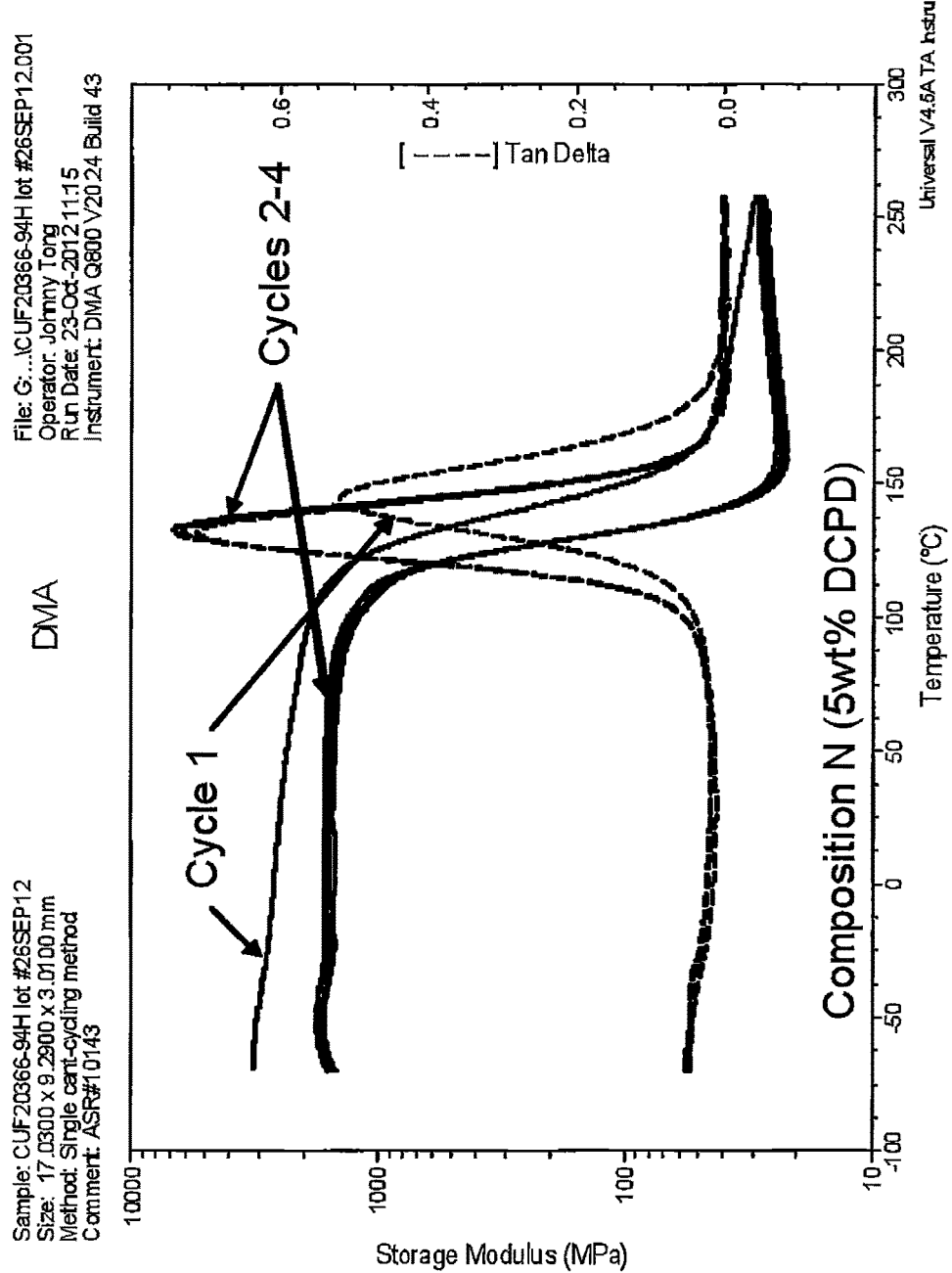
FIG. 8 depicts a trace of storage modulus over temperature for Sample N.
Figure 9:
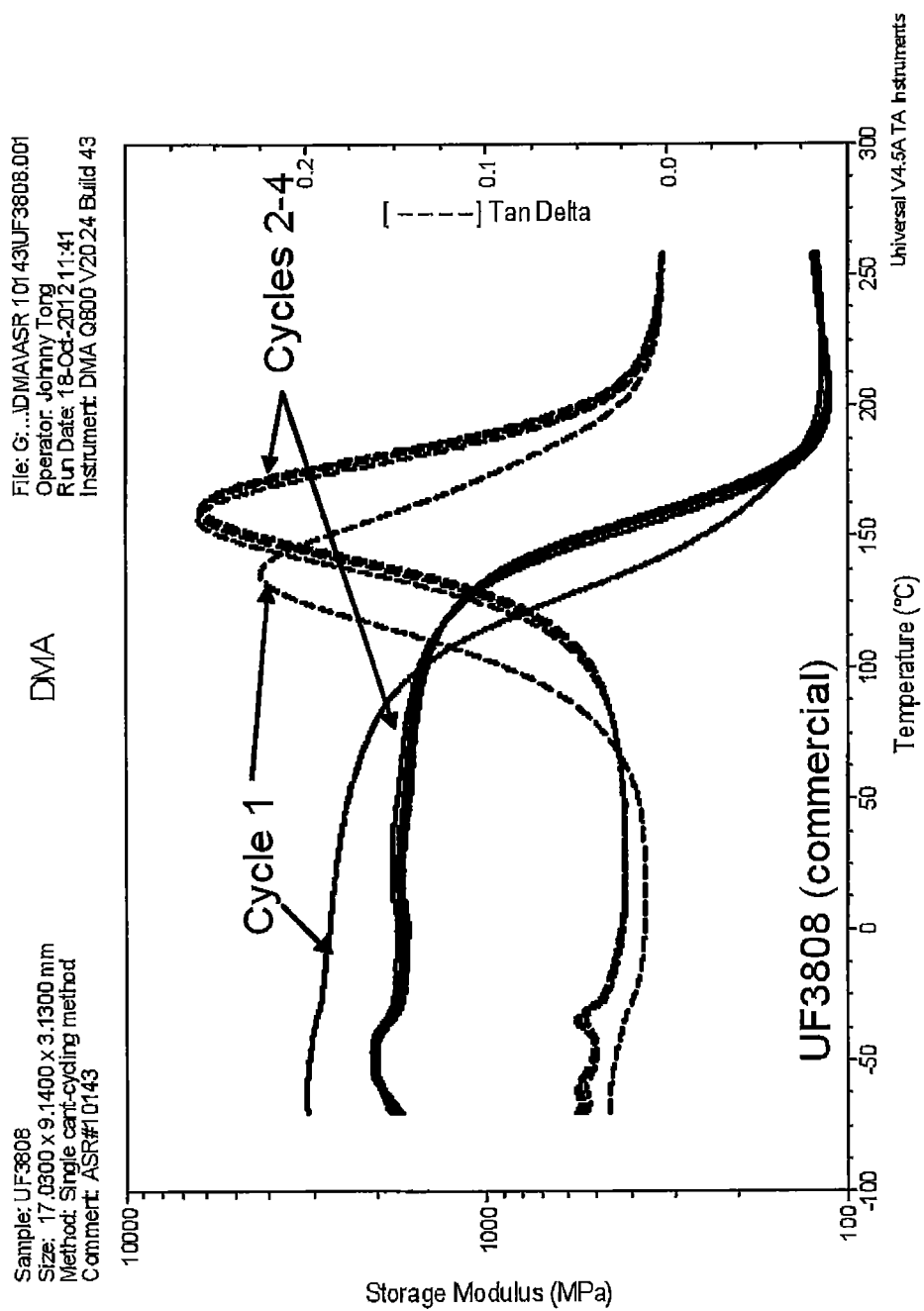
FIG. 9 depicts a trace of storage modulus over temperature for HYSOL UF3808.

Reference to FIGS. 6-8 shows the samples illustrated in Table 8, and FIG. 9 shows a modulus over temperature trace for HYSOL UF 3808.

The difference between the peak of the tan δ (glass transition temperature, or Tg) during cycle 1 and cycle 4, Δ tan δ, for the samples was calculated. The difference between the modulus at 25° C. during cycle 1 and cycle 4 for the samples was also calculated. For Samples K, L, and M, the respective Tgs were observed to decrease; the opposite was observed for HYSOL OF 3800 and HYSOL UF 3808.

The modulus decrease was observed to be more significant for Samples K, L, and M, than for HYSOL UF 3800 and HYSOL UF 3808.

Reference Table 9 below shows additional thermal cycling evaluations for two samples compared to the commercially available products, HYSOL UF 3800 and HYSOL UF 3808. One thermal cycling condition (Thermal Cycling 1) was performed from a temperature of −40° C. to 85° C., 30 minutes per cycle; another thermal cycling (Thermal Cycling 2) was performed from a temperature of −55° C. to 125° C., 30 minutes per cycle. The components used were 6×6 mm WL-CSP.

TABLE 9

| Sample | Thermal Cycling (1) - first failure | Thermal Cycling (2) - first failure | Tg by TMA (° C.) |
|---|---|---|---|
| HYSOL UF 3800 | <600 | | 69 |
| HYSOL UF 3808 | <2800 | <1200 | 113 |
| B | | >1400 | 124 |
| F | >3000 | | 128 |

Rework

Figure 3:
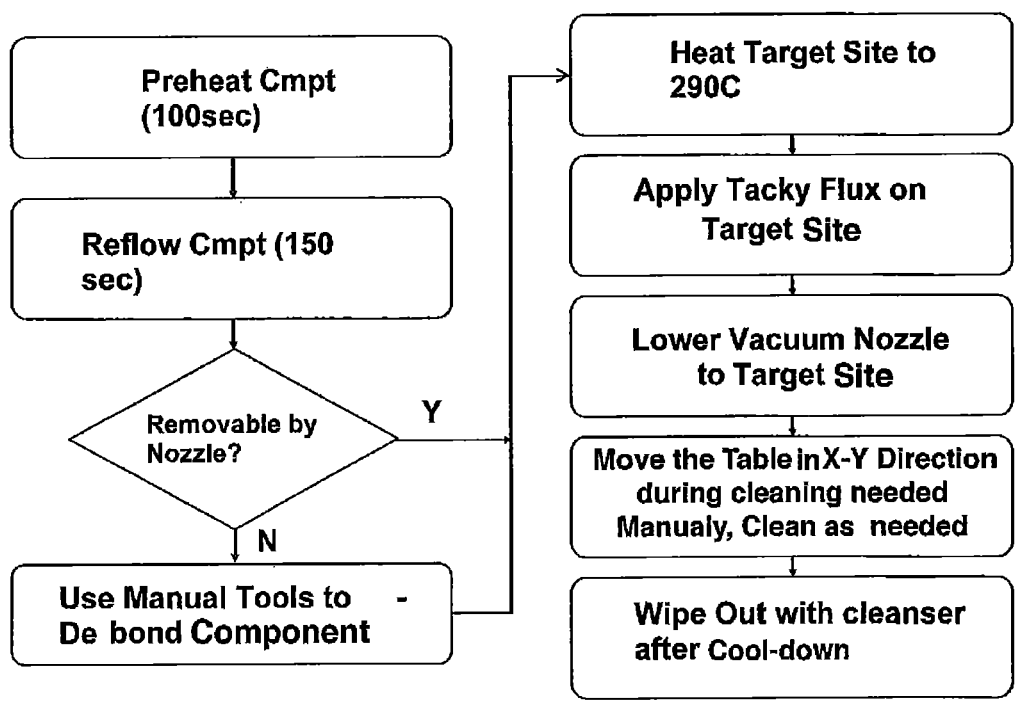
FIG. 3 depicts a flow diagram of a procedure useful to rework a cured thermosetting resin composition in accordance with the present invention, so as to remove a semiconductor device from a circuit board to which it had been attached.

Using a hot air generator, the area around the WL-CSP fixed to the circuit board with the samples was heated by applying hot air at a temperature of 285° C. for a period of time of 30 seconds. Then, the WL-CSP was removed by vacuum suction with an appropriate nozzle lifting the WL-CSP. The board was cleaned from any remaining cured reaction product residue by wiping the surface. Reference to FIG. 3 shows a flow diagram of the process.

What is claimed is:

1. A curable composition, reaction products of which are controllably degradable upon exposure to a temperature condition greater than a temperature condition used to cure the composition, comprising:
   (a) a curable resin component;
   (b) a curative and
   (c) a diene/dienophile couple functionalized with at least two groups reactive with the curable resin component, wherein the diene/dienophile couple is selected from

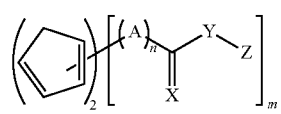

I wherein X is $CH_2$, O, S, or NR, wherein R is H, alkyl, aryl or aralkyl; Y is O, S or NR, wherein R is H, alkyl, aryl or aralkyl; A is alkylene; Z is H, (meth)acryloyl, glycidyl or a group containing polymerizable functionality; n is 0 or 1; and m is 2-4, and isomers thereof, and combinations thereof; or

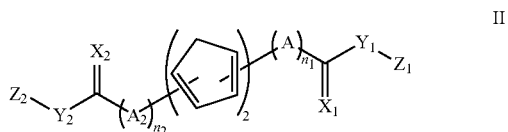

II wherein $X_1$ and $X_2$ are the same or different, and are each independently selected from $CH_2$, O, S, or NR, wherein R is H, alkyl, aryl or aralkyl; $Y_1$ and $Y_2$ are the same or different, and are each independently selected from O, S or NR, wherein R is H, alkyl, aryl or aralkyl; $A_1$ and $A_2$ are the same or different and are each independently alkylene; $Z_1$ and $Z_2$ are the same or different, and are each independently selected from H, (meth)acryloyl, glycidyl or one or more of groups containing polymerizable functionalities; and $n_1$ and $n_2$ are the same or different, and are each independently 0 or 1, wherein the curative is selected from one or more of imidazoles, dicyandimide, carboxylic acids, anhydrides, phenolic hardeners, amines, thiols, alcohols, and alkalines.

2. The composition of claim 1, wherein the curable resin component is a member selected from the group consisting of epoxy, episulfide, oxetane, thioxetane, oxazine, maleimide, itaconamide, nadimide, (meth)acrylate, (meth)acrylamide, and combinations thereof.

3. The composition of claim 1, wherein the two reactive groups are the same.

4. The composition of claim 1, wherein the two reactive groups are different.

5. The composition of claim 1, wherein the diene of the diene/dienophile couple is cyclopentadiene.

6. The composition of claim 1, wherein the dienophile of the diene/dienophile couple is cyclopentadiene.

7. The composition of claim 1, wherein the greater temperature condition is about 170° C. or greater.

8. The composition of claim 1, wherein the cure temperature condition is about 100° C. to about 150° C.

* * * * *

UNITED STATES PATENT AND TRADEMARK OFFICE
CERTIFICATE OF CORRECTION

PATENT NO. : 10,472,548 B2  
APPLICATION NO. : 15/795501  
DATED : November 12, 2019  
INVENTOR(S) : Timothy M. Champagne et al.

Page 1 of 1

It is certified that error appears in the above-identified patent and that said Letters Patent is hereby corrected as shown below:

In the Specification

Column 14, Line 51 change "NANOPDX" to --NANOPOX--.  
Column 14, Line 51 change "NANOPDX XP 22" to --NANOPOX XP 22--.  
Column 14, Line 52 change "NANOPDX" to --NANOPOX--.  
Column 14, Line 54 change "NANOPDX" to --NANOPOX--.  
Column 14, Line 56 change "NANOPDX XP 22" to --NANOPOX XP 22--.  
Column 14, Line 60 change "NANOPDX E" to --NANOPOX E--.  
Column 14, Line 61 change "NANOPDX E" to --NANOPOX E--.  
Column 14, Line 67 change "NANOPDX E" to --NANOPOX E--.  
Column 15, Line 18 change "NANOPDX E" to --NANOPOX E--.  
Column 15, Line 30 change "NANOPDX E" to --NANOPOX E--.  
Column 15, Line 36 change "NANOPDX E" to --NANOPOX E--.  
Column 15, Line 43 change "NANOPDX E" to --NANOPOX E--.  
Column 15, Line 47 change "NANOPDX E" to --NANOPOX E--.

Signed and Sealed this  
Thirteenth Day of April, 2021

Drew Hirshfeld  
*Performing the Functions and Duties of the*  
*Under Secretary of Commerce for Intellectual Property and*  
*Director of the United States Patent and Trademark Office*